(12) United States Patent
Boyle et al.

(10) Patent No.: US 10,144,726 B2
(45) Date of Patent: Dec. 4, 2018

(54) MODULATORS OF THE P70S6 KINASE FOR USE IN THE TREATMENT OF BRAIN DISORDERS AND TRIPLE-NEGATIVE BREAST CANCER

(71) Applicant: SENTINEL ONCOLOGY LIMITED, Cambridge (GB)

(72) Inventors: Robert George Boyle, Cambridge (GB); David Winter Walker, Cambridge (GB)

(73) Assignee: SENTINEL ONCOLOGY LIMITED, Cambridge (GB)

( * ) Notice: Subject to any disclaimer, the term of this patent is extended or adjusted under 35 U.S.C. 154(b) by 0 days.

(21) Appl. No.: 15/549,599

(22) PCT Filed: Feb. 15, 2016

(86) PCT No.: PCT/EP2016/053172
§ 371 (c)(1),
(2) Date: Aug. 8, 2017

(87) PCT Pub. No.: WO2016/131776
PCT Pub. Date: Aug. 25, 2016

(65) Prior Publication Data
US 2018/0022735 A1    Jan. 25, 2018

(30) Foreign Application Priority Data
Feb. 16, 2015 (GB) .................... 1502567.9

(51) Int. Cl.
*A61K 31/53* (2006.01)
*A61K 31/498* (2006.01)
*A61P 35/04* (2006.01)
*C07D 403/12* (2006.01)
*C07D 403/04* (2006.01)

(52) U.S. Cl.
CPC .......... *C07D 403/12* (2013.01); *A61K 31/498* (2013.01); *A61K 31/53* (2013.01); *A61P 35/04* (2018.01); *C07D 403/04* (2013.01)

(58) Field of Classification Search
CPC ....................................................... A61P 35/04
See application file for complete search history.

(56) References Cited

U.S. PATENT DOCUMENTS

2012/0071478 A1*   3/2012   Boyle .................. C07D 401/14
514/234.8

FOREIGN PATENT DOCUMENTS

WO         2010/136755 A1       12/2010

OTHER PUBLICATIONS

Lin et al., "CNS Metastases in Breast Cancer: Old Challenge, New Frontiers," Clin. Cancer Res. 19(23); 6404-18 (2013). (Year: 2013).*
Palmieri et al., "Brain Metastases of Breast Cancer," Breast Disease 26, 139-47 (2006,2007). (Year: 2006).*
International Search Report and Written Opinion for PCT/EP2016/053172 dated Apr. 18, 2016.
GB Search Report for GB Application No. GB1502567.9 dated Jun. 15, 2016.
Caccamo, A., et al., "Genetic Reduction of Mammalian Target of Rapamycin Ameliorates Alzheimer's Disease-Like Cognitive and Pathological Deficits by Restoring Hippocampal Gene Expression Signature", Neurobiology of Disease, Vo. 34, No. 23, pp. 7988-7998 (2014).
Bhattacharya, A., et al., "Genetic Removal of p70 S6 Kinase 1 Corrects Molecular, Synaptic, and Behavioral Phenotypes in Fragile X Syndrome Mice", Neuron, vol. 76, pp. 325-337 (2012).

(Continued)

*Primary Examiner* — Theodore R. West
(74) *Attorney, Agent, or Firm* — Heslin Rothenberg Farley & Mesiti P.C.

(57) ABSTRACT

The invention provides compounds for use in the treatment of a disease or condition selected from brain disorders and triple-negative breast cancer, the compounds being of the formula (1):

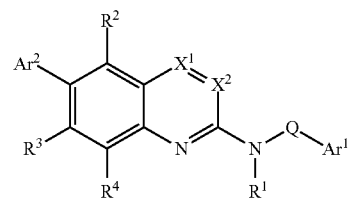

(1)

or a salt or tautomer thereof;
wherein:
$X^1$ is N or $N^+(O^-)$;
$X^2$ is N or CH;
Q is selected from a C1-3 alkylene group, cyclopropane-1,1-diyl and cyclobutane-1,1-diyl;
$R^1$ is selected from hydrogen and $C_{1-4}$ alkyl;
$R^2$, $R^3$ and $R^4$ are the same or different and each is selected from hydrogen and fluorine;
$Ar^1$ is a benzene, thiophene, naphthyl or pyridine ring optionally substituted with 1, 2 or 3 substituents selected from fluorine; chlorine; bromine; $C_{1-4}$ hydrocarbyl; $C_{1-4}$ hydrocarbyloxy; trifluoromethyl; difluoromethyl; cyano; trifluoromethoxy; difluoromethoxy;
$Ar^2$ is a monocyclic 5- or 6-membered heteroaryl ring containing 1, 2 or 3 heteroatom ring members selected from O, N and S and being optionally substituted with 1, 2 or 3 substituents selected from fluorine; $C_{1-4}$ hydrocarbyl; amino; mono-$C_{1-4}$ hydrocarbylamino and di-$C_{1-4}$ hydrocarbylamino;
and wherein, in each substituent consisting of or containing $C_{1-4}$ hydrocarbyl, the $C_{1-4}$ hydrocarbyl is selected from $C_{1-4}$ alkyl, $C_{2-4}$ alkenyl, $C_{2-4}$ alkynyl, cyclopropyl, cyclobutyl and cyclopropylmethyl.

20 Claims, 3 Drawing Sheets

(56) References Cited

OTHER PUBLICATIONS

Pelicano, H., et al., "Mitochondrial dysfunction in some triple-negative breast cancer cell lines: role of mTOR pathway and therapeutic potential", Breast Cancer Research, vol. 16, No. 434, pp. 1-16 (2014).

Segatto, I., et al., "p70S6 kinase mediates breast cancer cell survival in response to surgical would fluid stimulation", Molecular Oncology, vol. 8, pp. 766-780 (2014).

Segatto, I., et al., "Inhibition of breast cancer local relapse by targeting p70S6 kinase activity", Journal of Molecular Cell Biology, vol. 5, pp. 428-431 (2013).

Khotskaya, Y.B., et al., "S6K1 promotes invasiveness of breast cancer cells in a model of metastasis of triple-negative breast cancer", American Journal of Translational Research, vol. 6, No. 4, pp. 361-376 (2014).

\* cited by examiner

MODULATORS OF THE P70S6 KINASE FOR USE IN THE TREATMENT OF BRAIN DISORDERS AND TRIPLE-NEGATIVE BREAST CANCER

CROSS REFERENCE TO RELATED APPLICATIONS

This application is a national stage filing under section 371 of International Application No. PCT/EP2016/053172, filed on Feb. 15, 2016, and published on Aug. 25, 2016 as WO 2016/131776, which claims priority to Great Britain Application No. 1502567.9, filed on Feb. 16, 2015. The entire contents of each of said applications are hereby incorporated herein by reference.

This invention relates to compounds that inhibit or modulate the activity of p70S6 kinase, pharmaceutical compositions containing the compounds and the therapeutic uses of the compounds.

BACKGROUND OF THE INVENTION

The enzyme, p70S6 kinase (also known as p70S6K, p70S6K1, pS6K, S6K, S6K1) is a serine-threonine kinase and a member of the AGC family. It is a downstream effector of the phosphatidylinositol 3 kinase (PI3K)/AKT/mammalian target of rapamycin (mTOR) signaling pathway and p70S6 undergoes phosphorylation and activation in response to growth factors such as IGF-I, EGF, TGF-[alpha] and HGF.

Activation of p70S6K in turn phosphorylates Ribosomal protein S6 (RPS6) which promotes translation leading to an increase in protein synthesis in a cell. High levels of protein synthesis are required for cellular proliferation. It has also been shown that p70S6K has a necessary role in the mitotic cycle of a cell (Lane et al, Nature, 1993, 363(6425):170-2).

The kinase p70S6K has been shown to be constitutively activated in human tumour cells, leading to tumour cell proliferation. Inhibition of the p70S6K/mTOR pathway has been shown to lead to a decrease in tumour cell proliferation and an increase in tumour cell apoptosis (Pene et al (2002) Oncogene 21, 6587 and Le et al (2003) Oncogene 22, 484). Inhibition of p70S6K activity would therefore present an attractive approach for the treatment of cancer.

The mTOR/p70S6K pathway has been shown to be activated in renal cell carcinoma and is inhibited by CCI-779 (Robb, V. A.; Karbowniczek, M.; Klein-Szanto, A. J.; Henske, E. P. *J Urol* 2007, 177, 346-52). Furthermore, patients with gliobastoma multiforme whose tumours express high levels of phosphorylated p70S6K have been found to benefit from treatment with CCI-779 (Galanis et al. *J Clin Oncol* 2005, 23, 5294-304).

In addition, a significant linear association between time to disease progression and inhibition of p70S6K activity in peripheral blood mononuclear cells (PBMCs) following administration of the mTOR inhibitor CCI-779 has been reported for Renal Cell Carcinoma patients by Peralba et al [(2003) Clinical Cancer Research 9, 2887]. This indicates that activity of p70S6K is a driver of disease in this setting and that p70S6K activity can be potentially be used as a clinical biomarker.

The gene RPS6KB1 that codes for p70S6K, is localized to chromosomal region 17q23 and this region is amplified in Breast Cancer (Cancer Res. (1999) 59: 1408-1 1—Localization of pS6K to Chromosomal Region 17q23 and Determination of Its Amplification in Breast Cancer). This leads to over-expression of p70S6K protein and a statistically significant association between amplification and poor prognosis has been observed in breast cancer patients (Detecting activation of ribosomal protein S6 kinase by complementary DNA and tissue microarray analysis. J Natl Cancer Inst 2000; 92:1252-9).

Furthermore, Belletti et al published that S6K1 mediates survival and recurrence of Breast Cancer following surgery (Mol Oncol. 2014 May; 8(3):766-80).

P70S6K has a role in migration and invasion of ovarian cancer (p70 S6 kinase in the control of actin cytoskeleton dynamics and directed migration of ovarian cancer cells, Oncogene (2011), 1-13). In addition, it has been revealed that p70S6K has a role in promoting invasion, migration and metastasis of highly aggressive Triple-Negative Breast Cancer cells (Targeting p70S6K Prevented Lung Metastasis in a Breast Cancer Xenograft Model, Akar et al, Molecular Cancer Therapeutics (2010), 9 (5), 1180 and Hung et al, S6K1 promotes invasiveness of breast cancer cells in a model of metastasis of triple-negative breast cancer, Am. J. Transl. Res. 2014 Jul. 18; 6(4):361-76).

In addition, Lymphangioleiomyomatosis (LAM) is a disease typified by hyper-activation of the PI3K/Akt/mTOR/p70S6K axis due to mutation inactivation of the repressor complex, Tuberous Sclerosis Complex (TSC). LAM cells are also metastatic, giving rise to metastasis in the lung.

LAM is a rare destructive lung disease, almost exclusively of women, and is associated with the metastasis of tuberin-null cells (Taveira-DaSilva et al. (2006). Cancer Control. 2006; 13:276-285). Metastatic lesions develop in distant organs including lungs, kidney and lymph nodes, representing a severe and debilitating disease burden.

LAM occurs either sporadically or as a manifestation of Tuberous Sclerosis Complex (TSC), a dominant autosomal inherited disorder (Expert review on http://www.orpha.net). LAM and TSC disorders are characterized by nullifying mutations in tumour suppressors TSC1 or TSC2 leading to hyper activation of mTOR and of S6K1. This in turn drives cell growth & proliferation of LAM cells (Holz et al. (2014), Cell Cycle 2014; 13:371-382).

S6K1 is also known to promote metastasis in other cancers: breast (Akar et al. (2010), Mol Cancer Ther; 9(5) May 2010) and ovarian (Wong et al. (2011), Oncogene (2011) 30, 2420-2432). Due to the reliance of LAM cells on S6K1, and of the likely role of S6K1 in the metastatic process, it is anticipated that an S6K1 inhibitor will have disease-modifying properties for LAM.

Sporadic LAM has a prevalence of approx. 1 in 125,000 births whereas Pulmonary LAM, arising from TSC, has a prevalence of approx. 1 in 15,000 births (figures from internet rare disease database, http://www.orpha.net). No approved therapies exist for LAM and hence LAM is currently classified as an orphan disease.

Given that p70S6K promotes translation, it is known that p70S6K has a crucial role in the pathology of diseases that rely on excessive protein synthesis (for example, Fragile X Syndrome, Genetic Removal of p70 S6 Kinase 1 Corrects Molecular, Synaptic, and Behavioral Phenotypes in Fragile X Syndrome Mice. Klann et al, Neuron, Volume 76, Issue 2, p325-337, 18 Oct. 2012). Furthermore, p70S6K has a role in the pathology of cancers involving synthesis of oncogenic proteins such as c-Myc e.g. pancreatic cancer (The mTORC1/S6K1 Pathway Regulates Glutamine Metabolism through the eIF4B Dependent Control of c-Myc Translation, Blenis et al, Current Biology, Volume 24, Issue 19, p2274-2280, 6 Oct. 2014). For treatment of these conditions it would be advantageous to use an orally bioavailable p70S6K inhibitor to correct the excessive protein synthesis.

P70S6K has been implicated in the pathology of a number of cancers of the brain. Such conditions include, but are not limited to:

Brain metastases arising from cancers elsewhere in the body, for example brain metastases arising from a breast cancer such as Triple-Negative Breast Cancer (Distant metastasis in triple-negative breast cancer. Neoplasma 2013; 60: 290-294)

Brain metastases from metastatic breast cancer (Central nervous system or brain metastases traditionally occur in 10-16% of metastatic breast cancer patients and are associated with a dismal prognosis—see Breast Dis. 2006-2007; 26:139-47.)

Gliomas and Glioblastomas (S6K1 Plays a Key Role in Glial Transformation, Cancer Research (2008), 68(16), 6516-6523)

Furthermore, a p70S6K inhibitor may be particularly useful for treating the following cancers which are reliant on p70S6K signaling:

Bladder cancer
Breast cancer
Colo-rectal cancer (CRC)
Diffuse large B-cell lymphomas (DLBCL)
Gallbladder cancer
Head and Neck cancers
Hepatocellular carcinoma
Human Olfactory Neuroblastoma
Leukaemias
Lymphomas
Nasopharyngeal carcinoma
Neuroendocrine cancer
Non-Small Cell Lung Cancer (NSCLC)
Ovarian cancer
Pancreatic cancer
Pheochromocytoma
Renal Cell Carcinoma (RCC)
Squamous cell carcinoma
Metastases, for example bone metastases and lung metastases P70S6K also has a crucial role in the pathology of a number of neurodevelopmental diseases (many referenced in The Autistic Neuron: Troubled Translation?. Bear et al, Cell 135, Oct. 31, 2008). In particular, these diseases are caused by the excessive protein synthesis that is driven by P70S6K. Such conditions include, but are not limited to:

Fragile X Syndrome, a rare neuro-developmental disease caused by excessive levels of p70S6K activity
Autism and Autism Spectrum Disorders
Fragile X-associated tremor/ataxia syndrome (FXTAS)
Angleman's syndrome
Tuberous sclerosis
PTEN hamartoma syndrome
MECP2 duplication syndrome
Neurofibromatosis
Alzheimer's Disease (refer to (1) Oddo et al, Reducing Ribosomal Protein S6 Kinase 1 Expression Improves Spatial Memory and Synaptic Plasticity in a Mouse Model of Alzheimer's Disease, The Journal of Neuroscience, Oct. 14, 2015, 35(41):14042-14056 and (2) Genetic reduction of mammalian target of rapamycin ameliorates Alzheimer's disease-like cognitive and pathological deficits by restoring hippocampal gene expression signature, Journal of Neuroscience (2014), 34(23), 7988-7998)
Down Syndrome (mTOR Hyperactivation in Down Syndrome Hippocampus Appears Early During Development, Journal of Neuropathology & Experimental Neurology (2014), 73(7), 671-683)

PTEN Hamartoma Syndrome

PTEN hamartoma tumour syndrome (PHTS) encompasses four major clinically distinct syndromes associated with germline mutations in the tumour suppressor PTEN. These allelic disorders, Cowden syndrome, Bannayan-Riley-Ruvalcaba syndrome, Proteus syndrome, and Proteus-like syndrome are associated with unregulated cellular proliferation leading to the formation of hamartomas (benign and malignant tumours of the thyroid, breast, and endometrium) (Genetics in Medicine (2009) 11, 687-694). The absence of PTEN leads to loss of down-regulation of phosphorylated Akt which in turn allows for unchecked survival, growth and proliferation of the cells in question. As S6K1 is a key effector of Akt, an S6K1 inhibitor may have utility in controlling the growth of the cancer. Prevalence of PHTS is currently unknown.

Neurofibromatosis Type 1

Neurofibromatosis type 1 is a condition characterized by changes in skin colouring (pigmentation) and the growth of tumours along nerves in the skin, brain, and other parts of the body. The signs and symptoms of this condition vary widely among affected people. Most adults with neurofibromatosis type 1 develop neurofibromas, which are noncancerous (benign) tumours that are usually located on or just under the skin. These tumours may also occur in nerves near the spinal cord or along nerves elsewhere in the body. Some people with neurofibromatosis type 1 develop cancerous tumours that grow along nerves. These tumours, which usually develop in adolescence or adulthood, are called malignant peripheral nerve sheath tumours. People with neurofibromatosis type 1 also have an increased risk of developing other cancers, including brain tumours and cancer of blood-forming tissue (leukemia).

Neurofibromatosis type 1 occurs in 1 in 3,000 to 4,000 people worldwide and currently surgery is the main treatment option; it is classed as an orphan disease as no targeted therapies exist (http://ghr.nlm.nih.gov/condition/neurofibromatosis-type-1)

Mutations in the NF1 gene cause neurofibromatosis type 1. The NF1 gene provides instructions for making neurofibromin protein. This protein is produced in many cells, including nerve cells and specialized cells surrounding nerves (oligodendrocytes and Schwann cells). Neurofibromin acts as a tumour suppressor. Mutations in the NF1 gene lead to the production of a non-functional version of neurofibromin that cannot regulate cell growth and division. As a result, tumours such as neurofibromas can form along nerves throughout the body. An S6K1 inhibitor may control growth of cells expressing mutated NF1 gene by dampening production of neurofibromin protein and other proteins essential to growth of the tumour.

Role of P70S6 in Neurological Diseases

P70S6K also has a crucial role in the pathology of a number of neurodevelopmental diseases (many referenced in The Autistic Neuron: Troubled Translation?. Bear et al, Cell 135, Oct. 31, 2008). In particular, these diseases are caused by the excessive protein synthesis that is driven by P70S6K.

It is well known that precise translation control (protein synthesis) is absolutely required for neurological processes of the brain such as long-lasting synaptic plasticity and the formation of long-term memory. Moreover, alterations in translational control are a common pathophysiological feature of human neurological disorders, including developmental disorders, neuropsychiatric disorders, and neurodegenerative diseases. Furthermore, it is known that translational control mechanisms are susceptible to modification by small molecules that penetrate the brain (Klann and Santini, Dysregulated mTORC1-dependent translational control: from brain disorders to psychoactive drugs, Front. Behav. Neurosci., 8 Nov. 2011, doi: 10.3389/fnbeh.2011.00076).

S6K1 is well known as a master regulator of protein biosynthesis via its role in translation initiation as well as phosphorylation and activation of various substrates that drive protein production (eIF4B, PDCD4, SKAR, eEF2K, RPS6—for review refer to Ma and Blenis, Nature Reviews Molecular Cell Biology 10, 307-318 (May 2009), doi: 10.1038/nrm2672).

The following disorders are typified by underlying aberrations in regulation of protein translation which is linked to the pathologies observed. An S6K1 inhibitor, which acts by reducing excessive protein translation may therefore have utility as a therapy in such disorders.

It is possible to classify certain disorders into sub-groups: (1) Neurodevelopmental Disorders (2) Neurodegenerative Diseases. Within each sub-class the disorders are linked by common themes:

1. Neurodevelopmental Disorders

Neurodevelopmental disorders are defined as diseases caused by abnormal development of the brain during the first two decades of life. It is possible to define a subgroup of these disorders that are characterized by single-gene mutations. A common molecular abnormality in several of these disorders is loss-of-function mutations and/or deletion of genes that encode proteins that normally repress mTORC1 signaling pathway. These disorders are listed below.

Fragile X Syndrome

Fragile X syndrome is a genetic condition that gives rise to a range of developmental problems including learning disabilities and cognitive impairment. Usually, males are more severely affected by this disorder than females, owing to the fact that the condition is inherited via the X-chromosome. Affected individuals usually have delayed development of speech and language by age 2. Most males with fragile X syndrome have mild to moderate intellectual disability, while about one-third of affected females are intellectually disabled. Children with fragile X syndrome may also have anxiety and hyperactive behavior such as fidgeting or impulsive actions. They may have attention deficit disorder (ADD), which includes an impaired ability to maintain attention and difficulty focusing on specific tasks. About one-third of individuals with fragile X syndrome have features of autism spectrum disorders that affect communication and social interaction. Seizures occur in about 15 percent of males and about 5 percent of females with fragile X syndrome. Most males and about half of females with fragile X syndrome have characteristic physical features that become more apparent with age. These features include a long and narrow face, large ears, a prominent jaw and forehead, unusually flexible fingers, flat feet, and in males, enlarged testicles (macroorchidism) after puberty. Fragile X syndrome occurs in approximately 1 in 4,000 males and 1 in 8,000 females.

Mutations in the FMR1 gene cause fragile X syndrome. The FMR1 gene provides instructions for making a protein called fragile X mental retardation 1 protein, or FMRP. This protein helps regulate the production of other proteins and plays a role in the development of synapses, which are specialized connections between nerve cells. Synapses are critical for relaying nerve impulses.

Nearly all cases of fragile X syndrome are caused by a mutation in which a DNA segment, known as the CGG triplet repeat, is expanded within the FMR1 gene. Normally, this DNA segment is repeated in the range between 5 and 44 times (more commonly either 29 or 30 times). In people with fragile X syndrome, however, the CGG segment is repeated more than 200 times. The abnormally expanded CGG segment turns off (silences) the FMR1 gene, which prevents the gene from producing FMRP.

FMRP is a repressor of protein translation. In the case of FXS patients, who either experience a loss or shortage of FMRP, there is no repression of translation, leading to excessive production of an array proteins normally controlled by FMRP. A number of these proteins are expressed in the neurons and control synaptic plasticity (memory formation, learning, ability to store information). Lack of control of production of these proteins leads to the neuropathological state observed in FXS patients. Klann et al published that S6K1 has a central role in the excessive translation of these proteins and that genetic knock-out of S6K1 resulted in correction of phenotypes in the mouse model of FXS (Genetic Removal of p70 S6 Kinase 1 Corrects Molecular, Synaptic, and Behavioral Phenotypes in Fragile X Syndrome Mice. Neuron 76, 325-337, 2012). It has been determined that S6K1 inhibitors described herein also have the ability to dampen protein synthesis in the neurons, leading to correction of aberrant phenotypes in a mouse model of FXS.

Furthermore, Tassone et al (Genes, Brain and Behavior (2012), doi: 10.1111/j.1601-183X.2012.00768.x) published that lymphocytes isolated from the blood of human FXS patients exhibited higher levels of phosphorylated (activated) p70S6K and also higher levels of phosphorylated RPS6, the direct substrate of S6K1. This confirms that p70S6K is more highly activated in human FXS patients and supports the notion of inhibiting p70S6K activity in order to correct the disease. In addition, this represents a possible clinical biomarker so as to assess the pharmacodynamics effect of the p70S6K inhibitor in the clinic.

Fragile X-associated Tremor/Ataxia Syndrome (FXTAS)

Fragile X-associated tremor/ataxia syndrome (FXTAS) is a rare neurodegenerative disorder characterized by adult-onset progressive intention tremor and gait ataxia. It is an X-linked genetic disorder and as such, the disease primarily affects males (Orphanet rare disease database, http://www.orpha.net/consor/cgi-bin/index.php?Ing=EN)

Prevalence is estimated at 1-9 in 100,000 individuals. The age of onset of tremor and/or ataxia in males is about 60 years. The clinical presentation is variable with dominant manifestations including: intention tremor, progressive cerebellar gait ataxia, frontal executive dysfunction, cognitive decline, peripheral neuropathy, and dysautonomia. Other signs include mild Parkinsonism and psychiatric manifestations (depression, anxiety, agitation) with possible progression to dementia. Carrier females generally have less severe manifestations than males but also have an increased risk of primary ovarian insufficiency, chronic muscle pain, and hypothyroidism. FXTAS is caused by a CGG trinucleotide repeat expansion (55-200 repeats) in the permutation range of the FMR1 gene. There is no specific treatment for FXTAS that targets the underlying pathological mechanism; FXTAS is therefore classed as an orphan disease. The CGG trinucleotide repeat expansion often leads to reduced levels of FMRP protein, a repressor of protein translation. This leads to excessive protein translation which may be counter-acted by use of an S6K1 inhibitor.

Autism and Autism Spectrum Disorders

Autism spectrum disorder (ASD) and autism are terms for a group of complex disorders of brain development. The disorders are characterized by difficulties in social interaction, verbal and nonverbal communication and repetitive behaviours. A publication in 2013 titled the Diagnostic and Statistical Manual of Mental Disorders (DSM-5) brought together all autism disorders into one umbrella diagnosis of ASD. Previously, they were recognized as distinct subtypes, including autistic disorder, childhood disintegrative disorder, pervasive developmental disorder-not otherwise specified (PDD-NOS) and Asperger syndrome. The U.S. Centers for Disease Control and Prevention (CDC) identify around 1 in 68 American children as on the autism spectrum. Studies also show that autism is four to five times more common among boys than girls. An estimated 1 out of 42 boys and 1 in 189 girls are diagnosed with autism in the United States. Overall, ASD affects over 3 million individuals in the U.S. and tens of millions worldwide (Autism Speaks website, http://www.autismspeaks.org/). Moreover, government autism statistics suggest that prevalence rates are on the increase. Fragile X syndrome (FXS) is the most common inherited cause of intellectual disabilities and the most common known cause of autism worldwide (Penagarikano et al (2007). The pathophysiology of Fragile X Syndrome. Annu. Rev. Genomics Hum. Genet. 8, 109-129). This causative link between FXS and autism indicates that an S6K1 inhibitor that exhibits efficacy in treating FXS may also be useful in treatment of autism and ASDs.

Angelman's Syndrome

Angelman's syndrome (AS) is a neurogenetic disorder that is usually diagnosed in infants and is characterized by developmental delay, severe intellectual disability, absent speech, exuberant behaviour with happy demeanor, motor impairment, and epilepsy. AS is caused by deficient UBE3A gene expression that may be caused by various abnormalities of chromosome 15 (Dan, B., Angelman syndrome: Current understanding and research prospects. Epilepsia, 2009. 50(11): p. 2331-2339). Although not precisely known, prevalence of AS among children and young adults is between 1/10,000 and 1/20,000 defining AS as a rare disease. Mutations in the E3 ubiquitin ligase UBE3A have been identified in AS, suggesting that ubiquitin-dependent protein turnover may be impaired in this disorder, possibly leading to elevated synaptic protein levels (Jiang and Beaudet, 2004). An S6K1 kinase inhibitor would exert its effect by reducing translation of synaptic protein levels.

Tuberous Sclerosis Complex

Tuberous sclerosis complex is a genetic disorder characterized by the growth of numerous noncancerous (benign) tumours in many parts of the body. These tumours can occur in the skin, brain, kidneys, and other organs, in some cases leading to significant health problems. Tuberous sclerosis complex also causes developmental problems, and the signs and symptoms of the condition vary from person to person.

Tuberous sclerosis complex often affects the brain, causing seizures, behavioral problems such as hyperactivity and aggression, and intellectual disability or learning problems. Some affected children have the characteristic features of autism, a developmental disorder that affects communication and social interaction. Benign brain tumours can also develop in people with tuberous sclerosis complex; these tumours can cause serious or life-threatening complications. Tuberous sclerosis complex affects about 1 in 6,000 people (http://ghr.nlm.nih.gov/condition/tuberous-sclerosis-complex)

Mutations in the TSC1 or TSC2 gene can cause tuberous sclerosis complex. The TSC1 and TSC2 genes provide instructions for making the proteins hamartin and tuberin, respectively. These proteins are involved in the signaling network of the PI3K pathway and act as tumour suppressors, inhibiting the activation of mTOR via Rheb-GTP. When TSC1 or TSC2 are mutated this leads to loss of tumour suppressor function, leading to mTOR hyper-activation.

Importantly, the mTORC1 inhibitor rapamycin has been shown to be effective in ameliorating learning and memory deficits in TSC2 heterozygous knockout mice (Ehninger et al., 2008b), suggesting that uncontrolled mTORC1 signaling is a core molecular mechanism involved in the behavioral abnormalities.

One of the functional effectors of mTOR is S6K1; therefore, inhibiting S6K1 function may have ameliorative effects in the disease MECP2 Duplication Syndrome MECP2 duplication syndrome is a genetic condition that is inherited in an X-linked pattern and occurs almost exclusively in males. It is characterized by moderate to severe intellectual disability. Most people with this condition also have weak muscle tone in infancy, feeding difficulties, poor or absent speech, seizures that may not improve with treatment or muscle stiffness (spasticity). Individuals with MECP2 duplication syndrome have delayed development of motor skills such as sitting and walking. Many individuals with MECP2 duplication syndrome have recurrent respiratory tract infections. These respiratory infections are a major cause of death in affected individuals, with almost half succumbing by age 25. The prevalence of MECP2 duplication syndrome is unknown; approximately 120 affected individuals have been reported in the scientific literature. MECP2 duplication syndrome arises due to a duplication of the MECP2 gene which leads to excessive production of MeCP2 protein in the brain. MeCP2 is a regulator of expression of other genes. Whilst MeCP2 is critical for normal brain function, an excess can lead to abnormal regulation of the target genes (http://ghr.nlm.nih.gov/condition/mecp2-duplication-syndrome). An S6K1 inhibitor may reduce production of MeCP2 protein via global dampening of translation and may have utility as therapeutic intervention in this disease.

Down Syndrome

Down syndrome (DS) or Down's syndrome, also known as trisomy 21, is a genetic disorder caused by the presence of all or part of a third copy of chromosome 21 (Patterson, D (July 2009). "Molecular genetic analysis of Down syndrome.". Human Genetics 126 (1): 195-214). It is typically associated with physical growth delays, characteristic facial features, and mild to moderate intellectual disability. DS is the most common chromosome abnormality in humans, occurring in about one per 1000 babies born each year (Weijerman, M E; de Winter, J P (December 2010). "Clinical practice. The care of children with Down syndrome.". European journal of pediatrics 169 (12): 1445-52).

Recent publications have identified that mTOR hyperactivation plays a role in DS in the early stages of development. In control (non-DS) hippocampi phosphorylated S6 was only detected prenatally; it became undetectable 2 months postnatally. Conversely, for DS patients, phosphorylated S6 and phosphorylated S6 kinase were detected prenatally and persisted throughout postnatal development. This was linked to increased expression of phosphorylated S6 protein (RPS6), phosphorylated p70S6K, phosphorylated eukaryotic initiation factor 4E binding protein 1, and phosphorylated mTOR in DS hippocampus compared with controls (J Neuropathol Exp Neurol. 2014 July; 73(7):671-83). Furthermore, it has been suggested that mTOR inhibitors such as Rapamycin or other Rapalogs may be of utility in treating Cognitive Deficits associated with DS (CNS Neurol Disord Drug Targets. 2014 February;13(1):34-40). As S6K1 controls phosphorylation and activation of S6 protein, an S6K1 inhibitor may be of therapeutic utility in counteracting the hyper-activated mTOR signaling in DS patients.

2. Neurodegenerative Diseases

Alzheimer's Disease

The clinical symptoms of Alzheimer disease (AD) include a gradual memory loss and subsequent dementia, and neuropathological deposition of senile plaques and neurofibrillary tangles. AD accounts for 60% to 70% of cases of dementia (Burns, A; Lliffe, S (5 Feb. 2009). "Alzheimer's disease."BMJ (Clinical research ed.) 338: b158). It is a devastating and relatively widespread disease—as of 2010, there were between 21 and 35 million people worldwide with AD ("Survival in dementia and predictors of mortality: a review". International journal of geriatric psychiatry 28 (11): 1109-24).

At the molecular level, AD is associated with (1) the progressive accumulation of amyloid β-peptides (Aβ) in the form of extracellular amyloid plaques in the human brain and (2) tau hyperphosphorylation. Recent publications have implicated the PI3K/mTOR signaling pathway in the pathogenesis of the disease. For example, genetic knock-out of mTOR protein in Tg2576 mice, a widely used animal model of AD, was found to suppress amyloid-β deposits and rescue memory deficits in the animals (J Neurosci. 2014 Jun. 4; 34(23):7988-98). Furthermore, testing of post-mortem brain tissue from human AD patients highlighted that alteration of mTOR signaling and autophagy occurs at early stages of AD, leading to a significant increase of Aβ (1-42) levels and hyper-activation of the PI3K/Akt/mTOR pathway (J Neurochem. 2015 Jan. 27). The expression level of S6K1, the mTOR downstream target, was increased in these samples suggesting that a therapeutic intervention by an S6K1 inhibitor may be of utility to control synthesis of amyloid β protein and to dampen signaling from mTOR. Furthermore, increased levels of phosphorylated mTOR and S6K1 were also found in some of the brain areas affected in AD, such as cortex, of double APP/PS1 transgenic mice, a model of AD (Lafay-Chebassier et al., 2005).

In addition, Oddo et al (Reducing Ribosomal Protein S6 Kinase 1 Expression Improves Spatial Memory and Synaptic Plasticity in a Mouse Model of Alzheimer's Disease, The Journal of Neuroscience, Oct. 14, 2015, 35(41):14042-14056) published data that supports the following conclusions: (1) S6K1 activity is upregulated in the brains of AD patients (2) in a mouse model of AD, S6K1 activity in brain is also higher than control (3) Genetic reduction of S6K1 in the AD model mouse (via haplodeficiency) (A) improved synaptic plasticity and spatial memory deficits, and (B) reduced accumulation of Amyloid-B (AB) and phospho-tau/total tau levels, the key neuropathological hallmarks of AD. This validation gives credence to the hypothesis that manipulation of S6K1 activity via a small molecule S6K1 inhibitor could be a valid therapeutic approach in AD.

Huntington's Disease

Huntington's disease is an inherited, progressive brain disorder that causes uncontrolled movements, emotional problems, and loss of thinking ability (cognition); there are two forms of the disease: (1) adult-onset Huntington's disease, the most common form of this disorder, which usually appears in a person's thirties or forties and (2) Juvenile-onset Huntington disease, which is less common and begins in childhood or adolescence. In both forms the disease is progressive with affected individuals usually living for only 10 to 15 years after signs and symptoms appear. Huntington's disease affects an estimated 3 to 7 people per 100,000 of European ancestry.

Huntington disease is caused by Mutations in the HTT gene which leads to production of an abnormally long version of the huntingtin protein. The elongated protein is cut into smaller, toxic fragments that bind together and accumulate in neurons, disrupting the normal functions of these cells. The dysfunction and eventual death of neurons in certain areas of the brain underlie the signs and symptoms of Huntington disease. Recent publications have shown that mutant Htt contributes to the pathogenesis of HD by enhancing mTORC1 activity (Sci. Signal., 28 Oct. 2014, Vol. 7, Issue 349, p. ra103).

One of the functional effectors of mTOR signaling is S6K1; therefore, inhibiting S6K1 function may have ameliorative effects in the disease. In addition, inhibiting S6K1 may limit the production of huntingtin protein via dampening of global protein translation.

Parkinson's Disease

Parkinson's disease (PD) is a progressive neurodegenerative condition resulting from the death of the dopamine-containing cells of the substantia nigra. People with PD classically present with the symptoms and signs associated with parkinsonism, namely bradykinesia, rigidity and rest tremor. PD is a common, chronic, progressive neurological condition, estimated to affect 100-180 people per 100,000 of the population (between 6 and 11 people per 6000 of the general population in the UK) and has an annual incidence of 4-20 per 100,000. There is a rising prevalence with age and a higher prevalence and incidence of PD in males (https://www.nice.org.uk/guidance/cg035/chapter/introduction).

Whilst PD traditionally has been considered a non-genetic disorder, at least 5% of people are now known to have forms of the disease that occur because of a mutation of one of several specific genes. Mutations in specific genes have been conclusively shown to cause PD. These genes code for alpha-synuclein (SNCA), parkin (PRKN), leucine-rich repeat kinase 2 (LRRK2 or dardarin), PTEN-induced putative kinase 1 (PINK1), DJ-1 and ATP13A2 (Lesage S, Brice A; Brice (April 2009). "Parkinson's disease: from monogenic forms to genetic susceptibility factors". Hum. Mol. Genet. 18 (R1): R48-59).

Recent studies addressing the mechanism of neurodegeneration in PD demonstrate the involvement of the mTORC1 signaling pathway in the survival mechanism of dopaminergic neurons. In vivo and in vitro studies show that degeneration induced by treatment with PD toxins, such as 6-OHDA and MPTP, leads to upregulation of RTP801, a protein encoded by a RTP801 stress-responsive gene, which in turn reduces mTOR kinase activity. It has been proposed that the molecular mechanism, linking high levels of RTP801 to mTORC1 inhibition and neurodegeneration involves TSC2 and Akt (Deyoung et al., 2008; Malagelada et al., 2008). Either genetic manipulations that interfere with TSC2 or increase the expression of a constitutively active form of Akt protected against the PD toxins and prevented the increase in RTP801 (Malagelada et al., 2008). However, rapamycin was reported as neuroprotective agent both in cell culture and in a MPTP mouse model (mouse model of PD). It was proposed that rapamycin may enhance Akt activity through inhibition of mTORC1-dependent activation of S6K1 and the subsequent reduction of phospho-IRS-1, which is a scaffold protein involved in the activation of PI3K and Akt (Shah et al., 2004). It therefore may also be the case that an inhibitor of S6K1 (a main effector of mTOR) will uncouple the same negative feedback loop to IRS-1, leading to activation of Akt and increased survival in the neurons of PD patients. An S6K1 inhibitor may therefore exhibit therapeutic effects when dosed to a PD patient.

For treatment of the above diseases it would be advantageous to use an orally bioavailable P70S6K inhibitor with properties allowing penetration of the brain in sufficient concentrations to achieve efficacy.

It would therefore be beneficial to develop compounds that have the ability to inhibit p70S6 kinase.

SUMMARY OF THE INVENTION

The present invention provides a class of arylalkylamino-substituted benzotriazines and quinoxalines, having activity as inhibitors of p70S6 kinase, for use in the treatment of brain disorders and certain cancers as described above, in particular triple negative breast cancer.

In one embodiment (Embodiment 1.0) of the invention, there is provided a compound for use in the treatment of a condition selected from brain disorders and triple-negative breast cancer, the compound being of the formula (1):

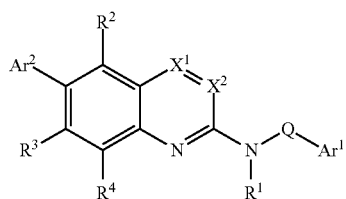

(1)

or a salt or tautomer thereof;
wherein:
$X^1$ is N or $N^+(O^-)$;
$X^2$ is N or CH;
Q is selected from a $C_{1-3}$ alkylene group, cyclopropane-1,1-diyl and cyclobutane-1,1-diyl;
$R^1$ is selected from hydrogen and $C_{1-4}$ alkyl;
$R^2$, $R^3$ and $R^4$ are the same or different and each is selected from hydrogen and fluorine;
$Ar^1$ is a benzene, thiophene, naphthyl or pyridine ring optionally substituted with 1, 2 or 3 substituents selected from fluorine; chlorine; bromine; $C_{1-4}$ hydrocarbyl; $C_{1-4}$ hydrocarbyloxy; trifluoromethyl; difluoromethyl; cyano; trifluoromethoxy; difluoromethoxy;
$Ar^2$ is a monocyclic 5- or 6-membered heteroaryl ring containing 1, 2 or 3 heteroatom ring members selected from O, N and S and being optionally substituted with 1, 2 or 3 substituents selected from fluorine; $C_{1-4}$ hydrocarbyl; amino; mono-$C_{1-4}$ hydrocarbylamino and di-$C_{1-4}$ hydrocarbylamino;
and wherein, in each substituent consisting of or containing $C_{1-4}$ hydrocarbyl, the $C_{1-4}$ hydrocarbyl is selected from $C_{1-4}$ alkyl, $C_{2-4}$ alkenyl, $C_{2-4}$ alkynyl, cyclopropyl, cyclobutyl and cyclopropylmethyl.

In a further embodiment (Embodiment 1.1) there is provided a compound for use in the treatment of a condition selected from brain disorders and triple-negative breast cancer, the compound being of the formula (1):

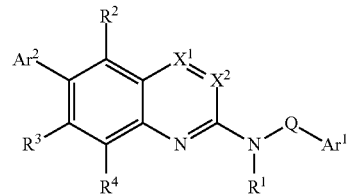

(1)

or a salt or tautomer thereof;
wherein:
$X^1$ is N or $N^+(O^-)$;
$X^2$ is N or CH;
Q is a $C_{1-3}$ alkylene group;
$R^1$ is selected from hydrogen and $C_{1-4}$ alkyl;
$R^2$, $R^3$ and $R^4$ are the same or different and each is selected from hydrogen and fluorine;
$Ar^1$ is a benzene, thiophene, naphthyl or pyridine ring optionally substituted with 1, 2 or 3 substituents selected from fluorine; chlorine; bromine; $C_{1-4}$ hydrocarbyl; $C_{1-4}$ hydrocarbyloxy; trifluoromethyl; difluoromethyl; cyano; trifluoromethoxy; difluoromethoxy;
$Ar^2$ is a monocyclic 5- or 6-membered heteroaryl ring containing 1, 2 or 3 heteroatom ring members selected from O, N and S and being optionally substituted with 1, 2 or 3 substituents selected from fluorine; $C_{1-4}$ hydrocarbyl; amino; mono-$C_{1-4}$ hydrocarbylamino and di-$C_{1-4}$ hydrocarbylamino;
and wherein, in each substituent consisting of or containing $C_{1-4}$ hydrocarbyl, the $C_{1-4}$ hydrocarbyl is selected from $C_{1-4}$ alkyl, $C_{2-4}$ alkenyl, $C_{2-4}$ alkynyl, cyclopropyl and cyclopropylmethyl.

The compounds of formula have good brain penetration and are therefore useful in treating various disorders of the brain where P70S6 kinase is implicated in the aetiology of the disorder. Examples of such disorders are set out below. The terms "brain disorder(s)" and "disorder(s) of the brain" are defined below in the section headed "Biological Activity". The compounds are also useful in the treatment of triple negative breast cancer.

Particular and preferred compounds of the formula (1) for use in the treatment of brain disorders and triple negative breast cancer are as defined in the following embodiments:

1.2 A compound for use according to Embodiment 1.0 or 1.1 wherein Q is $C_{1-2}$ alkylene.

1.3 A compound for use according to Embodiment 1.2 wherein Q is $CH_2$ or $CH(CH_3)$.

1.4 A compound for use according to Embodiment 1.3 wherein Q is $CH_2$.

1.5 A compound for use according to Embodiment 1.3 wherein Q is $CH(CH_3)$.

1.6 A compound for use according to Embodiment 1.5 wherein Q is in an R stereochemical configuration.

1.7 A compound for use according to any one of Embodiments 1.0 to 1.6 wherein $X^1$ is N.

1.8 A compound for use according to any one of Embodiments 1.0 to 1.6 wherein $X^1$ is $N^+(O^-)$.

1.9 A compound for use according to any one of Embodiments 1.0 to 1.8 wherein $X^2$ is N.

1.10 A compound for use according to any one of Embodiments 1.0 to 1.7 wherein $X^2$ is CH.

1.11 A compound for use according to any one of Embodiments 1.0 to 1.10 wherein $R^1$ is selected from hydrogen, methyl and ethyl.

1.12 A compound for use according to Embodiment 1.11 wherein $R^1$ is hydrogen.

1.13 A compound for use according to Embodiment 1.11 wherein $R^1$ is methyl.

1.14 A compound for use according to Embodiment 1.11 wherein $R^1$ is ethyl.

1.15 A compound according to any one of Embodiments 1.0 to 1.14 wherein $Ar^1$ is a benzene ring optionally substituted as defined in Embodiment 1.0.

1.16 A compound for use according to any one of Embodiments 1.0 to 1.16 wherein the optional substituents for $Ar^1$ are selected from fluorine, chlorine, methyl, methoxy, trifluoromethyl and trifluoromethoxy.

1.17 A compound for use according to Embodiment 1.16 wherein the optional substituents are selected from fluorine, chlorine, methyl and methoxy.

1.18 A compound for use according to any one of Embodiments 1.0 to 1.17 wherein $Ar^1$ is unsubstituted or substituted with one or two substituents.

1.19 A compound for use according to Embodiment 1.18 wherein $Ar^1$ is a phenyl ring which is unsubstituted or is substituted with one or two substituents wherein at least one substituent is present at the meta- or para-position of the phenyl ring.

1.20 A compound for use according to Embodiment 1.19 wherein $Ar^1$ is a phenyl ring which is unsubstituted; or is substituted with one substituent which is present at the meta- or para-position of the phenyl ring; or is substituted with two substituents which are present at meta- and para-positions of the phenyl ring.

1.21 A compound for use according to Embodiment 1.20 wherein $Ar^1$ is a phenyl ring which is unsubstituted.

1.22 A compound for use according to Embodiment 1.20 wherein $Ar^1$ is a phenyl ring which is substituted with one substituent which is present at the meta-position of the phenyl ring.

1.23 A compound for use according to Embodiment 1.20 wherein $Ar^1$ is a phenyl ring which is substituted with one substituent which is present at the para-position of the phenyl ring.

1.24 A compound for use according to Embodiment 1.20 wherein $Ar^1$ is a phenyl ring which is substituted with two substituents which are present at meta- and para-positions of the phenyl ring.

1.25 A compound for use according to Embodiment 1.20 wherein $Ar^1$ is selected from phenyl, 3-chlorophenyl, 3-fluorophenyl, 4-fluorophenyl, 3-methoxyphenyl, 3-methylphenyl and 3,4-difluorophenyl.

1.26 A compound for use according to Embodiment 1.25 wherein $Ar^1$ is phenyl.

1.27 A compound for use according to Embodiment 1.25 wherein $Ar^1$ is 3-chlorophenyl.

1.28 A compound for use according to Embodiment 1.25 wherein $Ar^1$ is 3-fluorophenyl.

1.29 A compound for use according to Embodiment 1.25 wherein $Ar^1$ is 4-fluorophenyl.

1.30 A compound for use according to Embodiment 1.25 wherein $Ar^1$ is 3-methoxyphenyl.

1.31 A compound for use according to Embodiment 1.25 wherein $Ar^1$ is 3-methylphenyl.

1.32 A compound for use according to Embodiment 1.25 wherein $Ar^1$ is 3,4-difluorophenyl.

1.33 A compound for use according to any one of Embodiments 1.0 to 1.32 wherein $R^2$ is hydrogen.

1.34 A compound for use according to any one of Embodiments 1.0 to 1.33 wherein $R^3$ is hydrogen.

1.35 A compound for use according to any one of Embodiments 1.0 to 1.34 wherein $R^4$ is hydrogen.

1.36 A compound for use according to any one of Embodiments 1.0 to 1.35 wherein $Ar^2$ is selected from pyrazole, imidazole, oxazole, isoxazole, thiazole, isothiazole, furan, thiophene, pyridine, pyrimidine, pyrazine, pyridazine, triazole, thiadiazole, furazan and oxadiazole rings each optionally substituted as defined in Embodiment 1.0.

1.37 A compound for use according to Embodiment 1.36 wherein $Ar^2$ is selected from pyrazole, imidazole, oxazole, isoxazole, thiazole, isothiazole, pyrimidine and pyridine rings, each optionally substituted as defined in Embodiment 1.0.

1.38 A compound for use according to Embodiment 1.37 wherein $Ar^2$ is selected from pyrazole, imidazole and pyridine rings, each optionally substituted as defined in Embodiment 1.0.

1.39 A compound for use according to Embodiment 1.38 wherein $Ar^2$ is an optionally substituted pyrazole ring.

1.40 A compound for use as defined in any one of Embodiments 1.0 to 1.39 wherein $Ar^2$ is unsubstituted or is substituted with one or two substituents selected from $C_{1-4}$ alkyl, cyclopropyl, cyclopropylmethyl, amino, mono-$C_{1-4}$ alkylamino and di-$C_{1-4}$ alkylamino.

1.41 A compound for use as defined in Embodiment 1.40 wherein $Ar^2$ is unsubstituted or is substituted with one or two substituents selected from methyl and amino.

1.42 A compound for use as defined in Embodiment 1.41 wherein $Ar^2$ is unsubstituted.

1.43 A compound for use as defined in Embodiment 1.41 wherein $Ar^2$ is substituted with one substituent.

1.44 A compound for use as defined in Embodiment 1.43 wherein the one substituent is selected from methyl and amino.

1.45 A compound for use as defined in Embodiment 1.44 wherein the one substituent is amino.

1.46 A compound for use as defined in Embodiment 1.44 wherein the one substituent is methyl.

1.47 A compound for use according to Embodiment 1.1 which is selected from:
Benzyl-[6-(1H-pyrazol-4-yl)-quinoxalin-2-yl]-amine;
Benzyl-methyl-[6-(1H-pyrazol-4-yl)-quinoxalin-2-yl]-amine;
(4-Chloro-benzyl)-[6-(1H-pyrazol-4-yl)-quinoxalin-2-yl]-amine;
(3-Chloro-benzyl)-[6-(1H-pyrazol-4-yl)-quinoxalin-2-yl]-amine;
(2-Chloro-benzyl)-[6-(1H-pyrazol-4-yl)-quinoxalin-2-yl]-amine;
(4-Fluoro-benzyl)-[6-(1H-pyrazol-4-yl)-quinoxalin-2-yl]-amine;
(3-Fluoro-benzyl)-[6-(1H-pyrazol-4-yl)-quinoxalin-2-yl]-amine;
(2-Fluoro-benzyl)-[6-(1H-pyrazol-4-yl)-quinoxalin-2-yl]-amine;
[6-(1H-Pyrazol-4-yl)-quinoxalin-2-yl]-pyridin-4-ylmethyl-amine;
[6-(1H-Pyrazol-4-yl)-quinoxalin-2-yl]-pyridin-3-ylmethyl-amine;
[6-(1H-Pyrazol-4-yl)-quinoxalin-2-yl]-pyridin-2-ylmethyl-amine;
(4-Methoxy-benzyl)-[6-(1H-pyrazol-4-yl)-quinoxalin-2-yl]-amine;
(3-Methoxy-benzyl)-[6-(1H-pyrazol-4-yl)-quinoxalin-2-yl]-amine;

(2-Methoxy-benzyl)-[6-(1H-pyrazol-4-yl)-quinoxalin-2-yl]-amine;
(4-Fluoro-3-trifluoromethyl-benzyl)-[6-(1H-pyrazol-4-yl)-quinoxalin-2-yl]-amine;
(4-Fluoro-benzyl)-methyl-[6-(1H-pyrazol-4-yl)-quinoxalin-2-yl]-amine;
Benzyl-methyl-(6-pyridin-4-yl-quinoxalin-2-yl)-amine;
Benzyl-methyl-(6-pyrimidin-4-yl-quinoxalin-2-yl)-amine;
((S)-1-Phenyl-ethyl)-[6-(1H-pyrazol-4-yl)-quinoxalin-2-yl]-amine;
Phenethyl-[6-(1H-pyrazol-4-yl)-quinoxalin-2-yl]-amine;
Benzyl-ethyl-[6-(1H-pyrazol-4-yl)-quinoxalin-2-yl]-amine;
(3-Methoxy-benzyl)-methyl-[6-(1H-pyrazol-4-yl)-quinoxalin-2-yl]-amine;
(3-Fluoro-benzyl)-methyl-[6-(1H-pyrazol-4-yl)-quinoxalin-2-yl]-amine;
(4-Fluoro-3-trifluoromethyl-benzyl)-methyl-[6-(1H-pyrazol-4-yl)-quinoxalin-2-yl]-amine;
[6-(1H-Pyrazol-4-yl)-quinoxalin-2-yl]-(3-trifluoromethoxy-benzyl)-amine;
(3,4-Difluoro-benzyl)-[6-(1H-pyrazol-4-yl)-quinoxalin-2-yl]-amine;
((R)-1-Phenyl-ethyl)-[6-(1H-pyrazol-4-yl)-quinoxalin-2-yl]-amine;
Benzyl-methyl-[7-(1H-pyrazol-4-yl)-benzo[1,2,4]triazin-3-yl]-amine;
Benzyl-methyl-[1-oxy-7-(1H-pyrazol-4-yl)-benzo[1,2,4]triazin-3-yl]-amine;
(3-Methoxy-benzyl)-[1-oxy-7-(1H-pyrazol-4-yl)-benzo[1,2,4]triazin-3-yl]-amine;
(3-Methoxy-benzyl)-[7-(1H-pyrazol-4-yl)-benzo[1,2,4]triazin-3-yl]-amine;
[6-(1H-Pyrazol-4-yl)-quinoxalin-2-yl]-thiophen-3-ylmethyl-amine;
Naphthalen-2-ylmethyl-[6-(1H-pyrazol-4-yl)-quinoxalin-2-yl]-amine;
[6-(1H-Pyrazol-4-yl)-quinoxalin-2-yl]-(4-trifluoromethyl-benzyl)-amine;
(3-Methyl-benzyl)-[6-(1H-pyrazol-4-yl)-quinoxalin-2-yl]-amine;
(2-Methyl-benzyl)-[6-(1H-pyrazol-4-yl)-quinoxalin-2-yl]-amine;
Benzyl-methyl-(6-pyrimidin-5-yl-quinoxalin-2-yl)-amine;
(4-Methyl-benzyl)-[6-(1H-pyrazol-4-yl)-quinoxalin-2-yl]-amine;
(2-Chloro-benzyl)-methyl-[6-(1H-pyrazol-4-yl)-quinoxalin-2-yl]-amine;
Benzyl-[6-(5-methyl-1H-pyrazol-4-yl)-quinoxalin-2-yl]-amine;
[(R)-1-(3-Fluoro-phenyl)-ethyl]-[6-(1H-pyrazol-4-yl)-quinoxalin-2-yl]-amine;
[(R)-1-(3-Methoxy-phenyl)-ethyl]-[6-(1H-pyrazol-4-yl)-quinoxalin-2-yl]-amine;
Methyl-((R)-1-phenyl-ethyl)-[6-(1H-pyrazol-4-yl)-quinoxalin-2-yl]-amine;
[(R)-1-(3-Fluoro-phenyl)-ethyl]-methyl-[6-(1H-pyrazol-4-yl)-quinoxalin-2-yl]-amine;
[(R)-1-(3-Methoxy-phenyl)-ethyl]-methyl-[6-(1H-pyrazol-4-yl)-quinoxalin-2-yl]-amine;
[(R)-1-(3-Chloro-phenyl)-ethyl]-[6-(1H-pyrazol-4-yl)-quinoxalin-2-yl]-amine;
[(R)-1-(3-Chloro-phenyl)-ethyl]-methyl-[6-(1H-pyrazol-4-yl)-quinoxalin-2-yl]-amine;
Methyl-((S)-1-phenyl-ethyl)-[6-(1H-pyrazol-4-yl)-quinoxalin-2-yl]-amine;
[6-(1H-Pyrazol-4-yl)-quinoxalin-2-yl]-((R)-1-m-tolyl-ethyl)-amine;
[(S)-1-(3-Fluoro-phenyl)-ethyl]-[6-(1H-pyrazol-4-yl)-quinoxalin-2-yl]-amine; and
[(S)-1-(3-Fluoro-phenyl)-ethyl]-methyl-[6-(1H-pyrazol-4-yl)-quinoxalin-2-yl]-amine;
1-oxido-N-[(1R)-1-phenylethyl]-7-(1H-pyrazol-4-yl)-1,2,4-benzotriazin-1-ium-3-amine; and
N-[(1R)-1-phenylethyl]-7-(1H-pyrazol-4-yl)-1,2,4-benzotriazin-3-amine;
and salts and tautomers thereof.

1.48 A compound for use according to Embodiment 1.47 which is selected from:
Benzyl-methyl-[6-(1H-pyrazol-4-yl)-quinoxalin-2-yl]-amine;
(4-Chloro-benzyl)-[6-(1H-pyrazol-4-yl)-quinoxalin-2-yl]-amine;
(3-Chloro-benzyl)-[6-(1H-pyrazol-4-yl)-quinoxalin-2-yl]-amine;
(4-Fluoro-benzyl)-[6-(1 H-pyrazol-4-yl)-quinoxalin-2-yl]-amine;
(3-Fluoro-benzyl)-[6-(1H-pyrazol-4-yl)-quinoxalin-2-yl]-amine;
(4-Methoxy-benzyl)-[6-(1 H-pyrazol-4-yl)-quinoxalin-2-yl]-amine;
(3-Methoxy-benzyl)-[6-(1H-pyrazol-4-yl)-quinoxalin-2-yl]-amine;
(4-Fluoro-benzyl)-methyl-[6-(1H-pyrazol-4-yl)-quinoxalin-2-yl]-amine;
((S)-1-Phenyl-ethyl)-[6-(1H-pyrazol-4-yl)-quinoxalin-2-yl]-amine;
Phenethyl-[6-(1H-pyrazol-4-yl)-quinoxalin-2-yl]-amine;
Benzyl-ethyl-[6-(1H-pyrazol-4-yl)-quinoxalin-2-yl]-amine;
(3-Methoxy-benzyl)-methyl-[6-(1H-pyrazol-4-yl)-quinoxalin-2-yl]-amine;
(3-Fluoro-benzyl)-methyl-[6-(1H-pyrazol-4-yl)-quinoxalin-2-yl]-amine;
(3,4-Difluoro-benzyl)-[6-(1H-pyrazol-4-yl)-quinoxalin-2-yl]-amine;
((R)-1-Phenyl-ethyl)-[6-(1H-pyrazol-4-yl)-quinoxalin-2-yl]-amine;
Benzyl-methyl-[7-(1H-pyrazol-4-yl)-benzo[1,2,4]triazin-3-yl]-amine;
Benzyl-methyl-[1-oxy-7-(1H-pyrazol-4-yl)-benzo[1,2,4]triazin-3-yl]-amine;
(3-Methoxy-benzyl)-[1-oxy-7-(1H-pyrazol-4-yl)-benzo[1,2,4]triazin-3-yl]-amine;
(3-Methoxy-benzyl)-[7-(1H-pyrazol-4-yl)-benzo[1,2,4]triazin-3-yl]-amine;
(3-Methyl-benzyl)-[6-(1H-pyrazol-4-yl)-quinoxalin-2-yl]-amine;
(4-Methyl-benzyl)-[6-(1H-pyrazol-4-yl)-quinoxalin-2-yl]-amine;
[(R)-1-(3-Fluoro-phenyl)-ethyl]-[6-(1H-pyrazol-4-yl)-quinoxalin-2-yl]-amine;
[(R)-1-(3-Methoxy-phenyl)-ethyl]-[6-(1H-pyrazol-4-yl)-quinoxalin-2-yl]-amine;
Methyl-((R)-1-phenyl-ethyl)-[6-(1H-pyrazol-4-yl)-quinoxalin-2-yl]-amine;
[(R)-1-(3-Fluoro-phenyl)-ethyl]-methyl-[6-(1H-pyrazol-4-yl)-quinoxalin-2-yl]-amine;
[(R)-1-(3-Methoxy-phenyl)-ethyl]-methyl-[6-(1H-pyrazol-4-yl)-quinoxalin-2-yl]-amine;
[(R)-1-(3-Chloro-phenyl)-ethyl]-[6-(1H-pyrazol-4-yl)-quinoxalin-2-yl]-amine;
[(R)-1-(3-Chloro-phenyl)-ethyl]-methyl-[6-(1H-pyrazol-4-yl)-quinoxalin-2-yl]-amine;
Methyl-((S)-1-phenyl-ethyl)-[6-(1H-pyrazol-4-yl)-quinoxalin-2-yl]-amine;

[6-(1H-Pyrazol-4-yl)-quinoxalin-2-yl]-((R)-1-m-tolyl-ethyl)-amine hydrochloride;

[(S)-1-(3-Fluoro-phenyl)-ethyl]-[6-(1H-pyrazol-4-yl)-quinoxalin-2-yl]-amine; and

[(S)-1-(3-Fluoro-phenyl)-ethyl]-methyl-[6-(1H-pyrazol-4-yl)-quinoxalin-2-yl]-amine;

1-oxido-N-[(1R)-1-phenylethyl]-7-(1H-pyrazol-4-yl)-1,2,4-benzotriazin-1-ium-3-amine; and N-[(1R)-1-phenylethyl]-7-(1H-pyrazol-4-yl)-1,2,4-benzotriazin-3-amine;

and salts and tautomers thereof.

1.49 A compound for use according to Embodiment 1.47 which is selected from:

Benzyl-methyl-[6-(1H-pyrazol-4-yl)-quinoxalin-2-yl]-amine;

(3-Chloro-benzyl)-[6-(1H-pyrazol-4-yl)-quinoxalin-2-yl]-amine;

(4-Fluoro-benzyl)-[6-(1H-pyrazol-4-yl)-quinoxalin-2-yl]-amine;

(3-Methoxy-benzyl)-[6-(1H-pyrazol-4-yl)-quinoxalin-2-yl]-amine;

(4-Fluoro-benzyl)-methyl-[6-(1H-pyrazol-4-yl)-quinoxalin-2-yl]-amine;

Benzyl-ethyl-[6-(1H-pyrazol-4-yl)-quinoxalin-2-yl]-amine;

(3-Fluoro-benzyl)-methyl-[6-(1H-pyrazol-4-yl)-quinoxalin-2-yl]-amine;

(3,4-Difluoro-benzyl)-[6-(1H-pyrazol-4-yl)-quinoxalin-2-yl]-amine;

((R)-1-Phenyl-ethyl)-[6-(1H-pyrazol-4-yl)-quinoxalin-2-yl]-amine;

((S)-1-Phenyl-ethyl)-[6-(1H-pyrazol-4-yl)-quinoxalin-2-yl]-amine;

Benzyl-methyl-[7-(1H-pyrazol-4-yl)-benzo[1,2,4]triazin-3-yl]-amine;

Benzyl-methyl-[1-oxy-7-(1H-pyrazol-4-yl)-benzo[1,2,4]triazin-3-yl]-amine;

[(R)-1-(3-Methoxy-phenyl)-ethyl]-[6-(1H-pyrazol-4-yl)-quinoxalin-2-yl]-amine;

Methyl-((R)-1-phenyl-ethyl)-[6-(1H-pyrazol-4-yl)-quinoxalin-2-yl]-amine;

Methyl-((S)-1-phenyl-ethyl)-[6-(1H-pyrazol-4-yl)-quinoxalin-2-yl]-amine;

[(R)-1-(3-Methoxy-phenyl)-ethyl]-methyl-[6-(1H-pyrazol-4-yl)-quinoxalin-2-yl]-amine

[(R)-1-(3-Chloro-phenyl)-ethyl]-[6-(1H-pyrazol-4-yl)-quinoxalin-2-yl]-amine;

[6-(1H-Pyrazol-4-yl)-quinoxalin-2-yl]-((R)-1-m-tolyl-ethyl)-amine hydrochloride;

Benzyl-[1-oxy-7-(1H-pyrazol-4-yl)-benzo[1,2,4]triazin-3-yl]-amine;

1-oxido-N-[(1R)-1-phenylethyl]-7-(1H-pyrazol-4-yl)-1,2,4-benzotriazin-1-ium-3-amine; and N-[(1R)-1-phenylethyl]-7-(1H-pyrazol-4-yl)-1,2,4-benzotriazin-3-amine;

and salts and tautomers thereof.

1.50 A compound for use according to any one of Embodiments 1.0 to 1.49 which is other than the compound N-[(1R)-1-(3-chlorophenyl)ethyl]-6-(1H-pyrazol-4-yl)quinoxalin-2-amine having the formula:

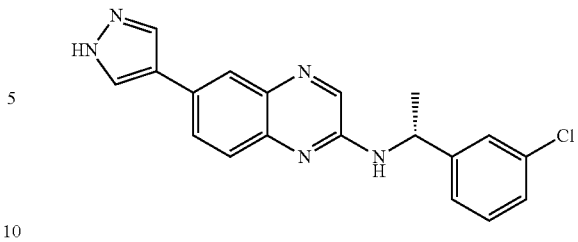

or a salt or tautomer thereof.

1.51 A compound for use according to Embodiment 1.0 or 1.1 which is the compound N-[(1R)-1-(3-chlorophenyl)ethyl]-6-(1H-pyrazol-4-yl)quinoxalin-2-amine having the formula:

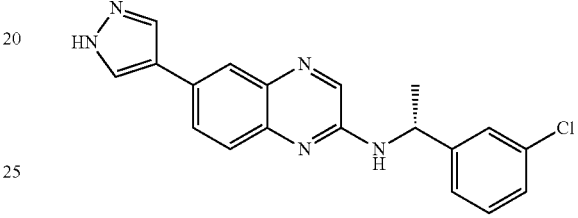

or a salt or tautomer thereof.

1.52 A compound for use according to any one of Embodiments 1.0 to 1.51 which is in the form of a salt.

1.53 A compound for use according to Embodiment 1.52 wherein the salt is an acid addition salt.

1.54 A compound for use according to any one of Embodiments 1.0 to 1.53 which is in the form of a solvate.

1.55 A compound for use according to Embodiment 1.54 wherein the solvate is a hydrate.

Novel Compounds

The compounds of Examples 18 and 19 below are novel compounds. Accordingly, in further embodiments (Embodiments 1.56 and 1.57), the invention provides:

1.56 The compound 1-oxido-N-[(1R)-1-phenylethyl]-7-(1H-pyrazol-4-yl)-1,2,4-benzotriazin-1-ium-3-amine and salts and tautomers thereof.

1.57 The compound N-[(1R)-1-phenylethyl]-7-(1H-pyrazol-4-yl)-1,2,4-benzotriazin-3-amine and salts and tautomers thereof.

Salts

The compounds of the formula (1) as defined in Embodiments 1.0 to 1.57 may be presented in the form of salts.

The salts referred to above (and also defined in Embodiment 1.52) are typically acid addition salts.

The salts can be synthesized from the parent compound by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free base form of the compound with the acid in water or in an organic solvent, or in a mixture of the two; generally, nonaqueous media such as ether, ethyl acetate, ethanol, isopropanol, or acetonitrile are used.

Acid addition salts (as defined in Embodiment 1.53) may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, (+)-L-lactic, (±)-DL-lactic, lactobionic, maleic, malic, (−)-L-malic, malonic, (±)-DL-mandelic, methanesulphonic, naphthalene-2-sulphonic, naphthalene-1,5-disulphonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, (+)-L-tartaric, thiocyanic, p-toluenesulphonic, undecylenic and valeric acids, as well as acylated amino acids and cation exchange resins.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci., Vol.* 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Geometric Isomers and Tautomers

The compounds of the formula (1) may exist in a number of different geometric isomeric, and tautomeric forms and references to the compounds of formula (1) as defined in Embodiments 1.0 to 1.57 include all such forms. For the avoidance of doubt, where a compound can exist in one of several geometric isomeric or tautomeric forms and only one is specifically described or shown, all others are nevertheless embraced by formula (1) or subgroups, subsets, preferences and examples thereof.

Optical Isomers

Where compounds of the formula contain one or more chiral centres, and can exist in the form of two or more optical isomers, references to the compounds include all optical isomeric forms thereof (e.g. enantiomers, epimers and diastereoisomers), either as individual optical isomers, or mixtures (e.g. racemic mixtures) or two or more optical isomers, unless the context requires otherwise.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4th Edition, John Wiley & Sons, New York, 1992, pages 109-114, and see also Cahn, Ingold & Prelog, *Angew. Chem. Int. Ed. Engl.,* 1966, 5, 385-415.

Optical isomers can be separated by a number of techniques including chiral chromatography (chromatography on a chiral support) and such techniques are well known to the person skilled in the art.

As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the invention exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound having one or more chiral centres, wherein at least 55% (e.g. at least 60%, 65%, 70%, 75%, 80%, 85%, 90% or 95%) of the compound of the formula (1) is present as a single optical isomer (e.g. enantiomer or diastereoisomer). In one general embodiment, 99% or more (e.g. substantially all) of the total amount of the compound of the formula (1) may be present as a single optical isomer (e.g. enantiomer or diastereoisomer).

Isotopes

The compounds of the invention as defined in any one of Embodiments 1.0 to 1.57 may contain one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$.

The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Solvates

Compounds of the formula (1) as defined in any one of Embodiments 1.0 to 1.57 may form solvates.

Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulphoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates.

Particularly preferred solvates are hydrates, and examples of hydrates include hemihydrates, monohydrates and dihydrates.

For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

Prodrugs

The compounds of the formula (1) as defined in any one of Embodiments 1.0 to 1.57 may be presented in the form of a pro-drug.

By "prodrugs" is meant for example any compound that is converted in vivo into a biologically active compound of the formula (1), as defined in any one of Embodiments 1.0 to 1.57.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any hydroxyl groups present in the parent compound with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LI DEPT, etc.). For example, the prodrug may be a sugar derivative or other glycoside conjugate, or may be an amino acid ester derivative.

Complexes and Clathrates

Also encompassed by formula (1) or subgroups, subsets, preferences and examples thereof are complexes (e.g. inclusion complexes or clathrates with compounds such as cyclodextrins, or complexes with metals) of the compounds.

Biological Activity

Compounds of the formula (1) as defined in any one of Embodiments 1.0 to 1.57 have activity as inhibitors of p70S6 kinase and exhibit good brain penetration.

As such, they may be useful in preventing or treating disorders of the brain in which p70S6 kinase or mutant forms thereof play an active part.

For example, P70S6K has been implicated in the pathology of a number of cancers of the brain. Such conditions include, but are not limited to:

Brain metastases from Triple-Negative Breast Cancer (Distant metastasis in triple-negative breast cancer. Neoplasma 2013; 60: 290-294)

Gliomas and Glioblastomas (S6K1 Plays a Key Role in Glial Transformation, Cancer Research (2008), 68(16), 6516-6523)

Triple-Negative Breast Cancer

The majority of breast cancers are hormone-positive breast cancers, wherein the growth of cancer cells is stimulated by exposure to oestrogen and/or progesterone. Patients suffering from such cancers are typically treated with therapeutic agents that prevent or reduce the formation of oestrogen (estrogen) in the body or prevent oestrogen from binding to the cell and stimulating growth. Examples of such therapeutic agents include selective estrogen-receptor response modulators (SERMs) such as tamoxifen and toremifene; aromatase inhibitors such as anastrozole, exemestane and letrozole; oestrogen-receptor downregulators (ERDs) such as fulvestrant; and luteinizing hormone-releasing hormone agents (LHRHs) such as goserelin, leuprolide), and triptorelin. The stimulation of progesterone on hormone-positive cancer cells is affected by estrogen receptor activity; therefore, if estrogen exposure is reduced, progesterone sensitivity is often also affected.

Approximately one quarter of breast cancers are HER2-positive breast cancers which are characterised by overexpression of human epidermal growth factor receptor 2 (HER2). HER2-positive cancers are typically treated with treated with therapeutic agents (e.g. Herceptin) that target the receptor to slow growth and replication.

There are however some breast cancers that are not oestrogen- or progesterone-positive and do not overexpress HER2 to a level that would characterise them as HER2-positive. Such forms of breast cancer are commonly referred to as triple-negative breast cancers. Patients with triple-negative breast cancer have fewer treatment options than patients with either hormone-positive or HER2-positive disease, and hence are generally more difficult to treat than oestrogen-positive, progesterone-positive and HER2-positive cancers. Triple negative breast cancers are also recognised as being more likely to spread (metastasize) to the brain. Patients with brain metastases are typically considered to be incurable with standard treatment approaches.

The compounds of formula (1) as defined in Embodiments 1.0 to 1.57 herein may be used in the treatment of triple negative breast cancer and the treatment of brain metastases arising from triple negative breast cancer. The compounds may also be used in the treatment of brain metastases arising from other forms of cancer.

Accordingly, in further Embodiments 2.1 to 2.9, the invention provides:

2.1 A compound as defined in any one of Embodiments 1.0 to 1.57 for use in the treatment of triple negative breast cancers.

2.2 A compound as defined in any one of Embodiments 1.0 to 1.57 for use in the treatment of brain metastases arising from triple negative breast cancers.

2.3 A compound as defined in any one of Embodiments 1.0 to 1.57 for use in the treatment of brain metastases arising from non-brain cancers.

2.4 The use of a compound as defined in any one of Embodiments 1.0 to 1.57 for the manufacture of a medicament for the treatment of triple negative breast cancers.

2.5 The use of a compound as defined in any one of Embodiments 1.0 to 1.57 for the manufacture of a medicament for the treatment of brain metastases arising from triple negative breast cancers.

2.6 The use of a compound as defined in any one of Embodiments 1.0 to 1.57 for the manufacture of a medicament for the treatment of brain metastases arising from non-brain cancers.

2.7 A method of treating a triple negative breast cancer in a subject (e.g. a human subject) in need thereof, which method comprises administering to the subject a therapeutically effective amount of a compound as defined in any one of Embodiments 1.0 to 1.57.

2.8 A method of treating brain metastases arising from triple negative breast cancers in a subject (e.g. a human subject) in need thereof, which method comprises administering to the subject a therapeutically effective amount of a compound as defined in any one of Embodiments 1.0 to 1.57.

2.9 A method of treating brain metastases arising from non-brain cancers in a subject (e.g. a human subject) in need thereof, which method comprises administering to the subject a therapeutically effective amount of a compound as defined in any one of Embodiments 1.0 to 1.57.

Gliomas

It is envisaged that the compounds of formula (1) as defined in Embodiments 1.0 to 1.57 herein will be useful in the treatment of gliomas on account of their potency as inhibitors of S6K1 (which is known to have a role in glial transformation) and their ability to reach the site of action, i.e. the brain.

Gliomas are a common type of primary brain tumour that originate in the glial cells in the brain, and account for about 30% of all primary brain and central nervous system tumours, and about 80% of all malignant brain tumours. Gliomas typically arise from three different types of cells that are normally found in the brain, namely astrocytes, oligodendrocytes, and ependymal cells. Major types of gliomas include ependymomas (associated with ependymal cells), astrocytomas (associated with astrocytes), oligodendrogliomas (associated with oligodendrocytes), brainstem glioma (which develops in the brain stem), optic nerve glioma (which develops in or around the optic nerve) and mixed gliomas (which contain cells from different types of glia).

An ependymoma is a type of glioma that develops from ependymal cells, usually in the lining of the ventricles of the brain or in the spinal cord. In children, they are most commonly found near the cerebellum. Ependymomas are rare, accounting for only about 2-3% of primary brain tumours. However, they account for about 8-10% of brain tumours in children and occur most often in children younger than 10 years of age.

Astrocytomas originate in the star-shaped glial cells (astrocytes) in the cerebrum. Astrocytomas do not usually spread outside the brain and spinal cord and do not usually affect other organs but they are the most common glioma and can occur in most parts of the brain and occasionally in the spinal cord. Two broad classes of astrocytoma are generally recognised, namely those with narrow zones of infiltration (mostly invasive tumours; e.g., pilocytic astrocytoma, subependymal giant cell astrocytoma, pleomorphic xanthoastrocytoma), that often are clearly outlined on diagnostic images; and those with diffuse zones of infiltration (e.g., high-grade astrocytoma, anaplastic astrocytoma, glioblastoma). Glioblastoma multiforme is a malignant astrocytoma and the most common primary brain tumour among adult humans.

An oligodendrogliomas is a type of glioma that develops from oliogodendrocytes, which are the supportive tissue cells of the brain, and are usually found in the cerebrum. About 4% of primary brain tumours are oliogodendrogliomas and they are most common in young and middle-aged adults. Seizures are a very common symptom of these gliomas, as well as headache, weakness, or changes in behavior or sleepiness.

Brain stem gliomas, as the name suggests, are tumours found in the brain stem. Most brain stem tumours cannot be surgically removed because of the remote location and delicate and complex function this area controls. Brain stem gliomas occur almost exclusively in children, typically in school-age children.

A mixed glioma is a malignant glioma made up of more than one type of glial cell. This type of glioma may also be referred to as an oligoastrocytoma. Mixed gliomas are often found in the cerebrum, but may metastasize to other parts of the brain. Only about 1% of primary brain tumours are mixed gliomas and they are most commonly found in adult men.

An optic nerve glioma is a type of malignant glioma (brain tumour) found in the optic chiasm. Optic nerve gliomas often surround the optic nerves, and are frequently found in people who have neurofibromatosis. A person suffering from an optic nerve glioma typically experiences loss of vision, and may also suffer from hormone disturbances as the tumours are often found at the base of the brain where the structures responsible for hormonal control are located. Optic nerve gliomas are typically difficult to treat because of the sensitivity of the surrounding brain structures.

In addition to being classified according to the type of glial cell from which they originate or the region of the brain in which they develop, gliomas can also be classified according to their "grade", which is a measure of the growth potential and aggressiveness of the tumour.

Thus, gliomas are most often referred to as "low-grade" or "high-grade" gliomas, the grade being determined by pathological evaluation of the tumour. Tumours can be further graded according to the World Health Organization (WHO) grading system, under which tumours are graded from I (least advanced disease—best prognosis) to IV (most advanced disease—worst prognosis).

Gliomas can also be classified according to whether they are located above or below the tentorium membrane which tentorium separates the cerebrum (above) region of the brain from the cerebellum (below). Supratentorial gliomas (i.e. tumours located above the tentorium in the cerebrum), are mostly found in adults (70%), whereas infratentorial gliomas (tumours located below the tentorium, in the cerebellum) are found mostly in children (70%).

A further class of gliomas consists of those tumours found in the pons of the brainstem. The brainstem has three parts (pons, midbrain and medulla); the pons controls critical functions such as breathing, making surgery on pontine gliomas extremely dangerous.

Accordingly, in further Embodiments 2.10 to 2.25, the invention provides:

2.10 A compound as defined in any one of Embodiments 1.0 to 1.57 for use in the treatment of gliomas and glioblastomas.

2.11 A compound for use according to Embodiment 2.10 wherein the glioma is an ependymoma.

2.12 A compound for use according to Embodiment 2.10 wherein the glioma is an astrocytoma.

2.13 A compound for use according to Embodiment 2.10 wherein the glioma is a glioblastoma.

2.14 A compound for use according to Embodiment 2.10 wherein the glioma is glioblastoma multiforme.

2.15 A compound for use according to Embodiment 2.10 wherein the glioma is an oligodendroglioma.

2.16 A compound for use according to Embodiment 2.10 wherein the glioma is a brainstem glioma.

2.17 A compound for use according to Embodiment 2.10 wherein the glioma is an optic nerve glioma.

2.18 A compound for use according to Embodiment 2.10 wherein the glioma is a mixed glioma.

2.19 A compound for use according to Embodiment 2.10 wherein the glioma is a low-grade glioma.

2.20 A compound for use according to Embodiment 2.10 wherein the glioma is a high-grade glioma.

2.21 A compound for use according to Embodiment 2.10 wherein the glioma is a supratentorial glioma.

2.22 A compound for use according to Embodiment 2.10 wherein the glioma is an infratentorial glioma.

2.23 A compound for use according to Embodiment 2.10 wherein the glioma is a pontine glioma.

2.24 The use of a compound as defined in any one of Embodiments 1.0 to 1.57 for the manufacture of a medicament for the treatment of a glioma as defined in any one of Embodiments 2.10 to 2.23.

2.25 A method of treating a glioma as defined in any one of Embodiments 2.10 to 2.23 in a subject in need thereof, which method comprises administering to the subject an effective therapeutic amount of a compound as defined in any one of Embodiments 2.10 to 2.23.

Neurodevelopmental Diseases and Neurodegenerative Diseases

As discussed above, P70S6K also has a crucial role in the pathology of a number of neurodevelopmental diseases and neurodegenerative disorders and diseases and it is envisaged that the inhibition of P70S6K will provide a means of treating many such diseases. Accordingly, in further embodiments 2.26 to 2.39, the invention provides:

2.26 A compound as defined in any one of Embodiments 1.0 to 1.57 for use in the treatment of a neurodevelopmental disorder.

2.27 A compound for use according to Embodiment 2.26 wherein the neurodevelopmental disorder is Fragile X Syndrome.

2.28 A compound for use according to Embodiment 2.26 wherein the neurodevelopmental disorder is Autism or an Autism Spectrum Disorder.

2.29 A compound for use according to Embodiment 2.26 wherein the neurodevelopmental disorder is Fragile X-associated tremor/ataxia syndrome (FXTAS).

2.30 A compound for use according to Embodiment 2.26 wherein the neurodevelopmental disorder is Angleman's syndrome.

2.31 A compound for use according to Embodiment 2.26 wherein the neurodevelopmental disorder is Tuberous sclerosis complex.

2.32 A compound for use according to Embodiment 2.26 wherein the neurodevelopmental disorder is MECP2 duplication syndrome.

2.33 A compound for use according to Embodiment 2.26 wherein the neurodevelopmental disorder is Down Syndrome.

2.34 A compound as defined in any one of Embodiments 1.0 to 1.57 for use in the treatment of a neurodegenerative disease.

2.35 A compound for use according to Embodiment 2.34 wherein the neurodegenerative disease is Alzheimer's disease.

2.36 A compound for use according to Embodiment 2.34 wherein the neurodegenerative disease is Huntington's disease.

2.37 A compound for use according to Embodiment 2.34 wherein the neurodegenerative disease is Parkinson's disease.

2.38 The use of a compound of the formula (1) as defined in any one of Embodiments 1.0 to 1.57 for the manufacture of a medicament for the treatment of a brain disorder, e.g. a brain disorder as defined in any one of Embodiments 2.26 to 2.37.

2.39 A method of treating a brain disorder (e.g. a brain disorder as defined in any one of Embodiments 2.26 to 2.37) in a subject (e.g. a mammalian subject such as a human), which method comprises administering to the subject a therapeutically effective amount of a compound of the formula (1) as defined in any one of Embodiments 1.0 to 1.57.

Other Diseases and Conditions in Which S6K1 may be Implicated

As discussed above, a P70S6K inhibitors may also be useful in the treatment of PTEN hamartoma syndrome and neurofibromatosis type 1. Accordingly, in further embodiments (Embodiments 2.40 to 2.43), the invention provides:

2.40 A compound as defined in any one of Embodiments 1.0 to 1.57 for use in the treatment of a condition which is PTEN hamartoma syndrome.

2.41 A compound as defined in any one of Embodiments 1.0 to 1.57 for use in the treatment of a condition which is neurofibromatosis type 1.

2.42 The use of a compound as defined in any one of Embodiments 1.0 to 1.57 for the manufacture of a medicament for the treatment of a condition as defined in either of Embodiments 2.40 and 2.41.

2.43 A method of treating a condition as defined in either of Embodiments 2.40 and 2.41 in a subject (e.g. a mammalian subject such as a human), which method comprises administering to the subject a therapeutically effective amount of a compound of the formula (1) as defined in any one of Embodiments 1.0 to 1.57.

Determination of Biological Properties

The ability of the compounds of the invention to inhibit P70S6 kinase can be determined by means of the protocols set out in the Examples section below.

The ability of the compounds of Embodiments 1.0 to 1.57 to inhibit cell proliferation can also be determined using the protocols set out in the Examples section below.

The compounds of the formula (1) are potent kinase P70S6 kinase inhibitors.

Preferred compounds of the formula (1) are those having an $IC_{50}$ against p70S6 kinase of less than 5 μM, or less than 1 μM and preferably less than 0.1 μM.

Accordingly, in further embodiments, the invention provides:

2.44 A compound for use according to any one of Embodiments 1.0 to 1.57 and 2.1 to 2.43 having an $IC_{50}$ against p70S6 kinase of less than 5 μM.

2.45 A compound for use according to any one of Embodiments 1.0 to 1.57 and 2.1 to 2.44 having an $IC_{50}$ against p70S6 kinase of or less than 1 μM.

2.46 A compound for use according to any one of Embodiments 1.0 to 1.57 and 2.1 to 2.45 having an an $IC_{50}$ against p70S6 kinase of less than 0.1 μM.

The compounds defined in Embodiments 1.0 to 1.57 have good brain penetration and therefore are useful in treating brain disorders in which inhibition of p70S6 kinase is therapeutically effective.

The activities of the compounds as P70S6 kinase inhibitors can be determined using the methods described in Examples 20(a) and 19(b) below.

The activity of the compounds against tumour cells and metastases can be determined using the methods described in Examples 20(c), 20(e) and 20(g) below.

The brain penetrating ability of the compounds of Embodiments 1.0 to 1.57 can be determined by means of the in vivo cassette mouse model described in Example 20(d) below. The mouse model is an industry-standard means of assessing brain penetration of small molecules (see for example "In vitro permeability analysis, pharmacokinetic and brain distribution study in mice of imperatorin, isoimperatorin and cnidilin" in Radix Angelicae Dahuricae, Fitoterapia, Volume 85, March 2013, Pages 144-153).

The activities of the compounds in an audiogenic seizure model of Fragile X Syndrome can be determined as described in Example 19 (e) below.

Methods for the Preparation of Compounds of the Invention

The compounds of the formula (1) can be prepared by the reaction schemes set out below and in the Examples.

For example, the compounds of Embodiments 1.0 to 1.57 can be prepared by a method which comprises:

(a) the reaction of a compound of the formula (10):

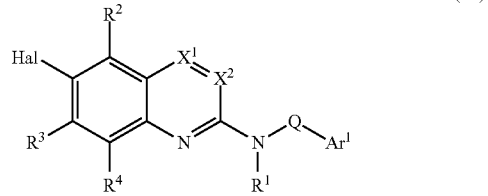

(10)

or an N-oxide thereof, wherein Hal is either bromine or chlorine, with a boronic acid or boronate reagent of the formula Ar²-Bor where Bor is a boronate or boronic acid residue, in the presence of a palladium catalyst; or (b) the reaction of a compound of the formula (11):

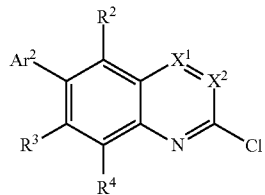

(11)

or a protected form thereof, with a compound of the formula Ar¹-Q-NR²H.

Reaction (a) above may be carried out under Suzuki coupling conditions, in the presence of a palladium catalyst such as bis(tri-t-butylphosphine)palladium (0) and a base (e.g. a carbonate such as potassium carbonate). The reaction may be carried out in a polar solvent such as dimethyl formamide (DMF), and the reaction mixture is typically subjected to heating, for example to a temperature in excess of 100° C.

Reaction (b) above may be carried out at room temperature in a polar solvent such as dimethyl sulphoxide or dimethyl formamide.

Illustrative reaction schemes for the preparation of compounds of the formula (1) are set out below.

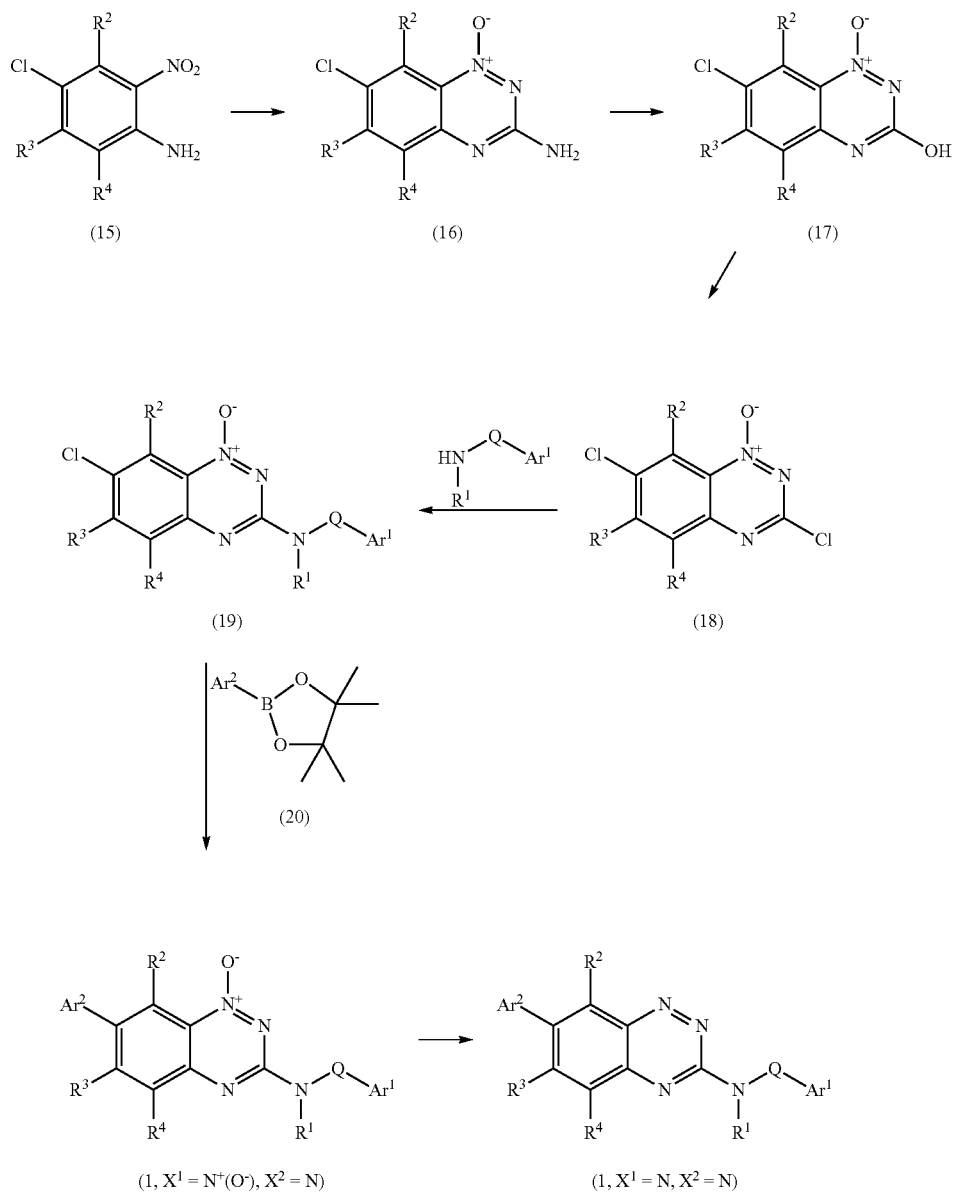

Scheme 1

Scheme 1 may be used to prepare benzotriazine compounds of the formula (1) in which X is N and N-oxides thereof.

In Scheme 1, the starting material is the chloronitroaniline (15) which is commercially available or can be prepared by by methods well known to the skilled chemist.

The chloronitroaniline (15) is reacted with cyanamide with heating (e.g. to a temperature of up to about 100° C.) to give the amino-benzotriazine N-oxide (16).

The amino-benzotriazine N-oxide (16) is diazotized with $NaNO_2$/HCl and the intermediate diazonium salt (not shown) is hydrolysed to form the hydroxybenzotriazine N-oxide compound (17). Reaction of the hydroxybenzotriazine N-oxide compound (17) with phosphorus oxychloride in the presence of a non-interfering base such as N,N-dimethylaniline gives the chlorobenzotriazine N-oxide compound (18). The chlorination reaction is typically carried out with heating, for example at reflux temperatures.

The chlorine atom at the 3-position of the benzotriazine ring is then displaced by a group $Ar^1$-Q-$NR^2$ by reaction with an amine compound of the formula $Ar^1$-Q-$NR^2$H to give the compound of formula (19). The displacement reaction may be carried out in a polar solvent such as DMF or DMSO, typically at room temperature.

The compound of formula (19) may then be reacted with a boronate or boronic acid derivative of the formula $Ar^2$-Bor where Bor is a boronate or boronic acid residue under Suzuki coupling conditions. In Scheme 1, $Ar^2$-Bor is exemplified by the boronic acid pinacol ester (20). The reaction is typically carried out with heating (e.g. to a temperature in the range 60-100° C.), in a polar solvent such as DMF in the presence of a palladium catalyst such as Fu's catalyst (bis(tri-t-butylphosphine)palladium (0)) and a base such as potassium carbonate or caesium carbonate.

Boronates and boronic acids of the formula $Ar^2$-Bor are widely available commercially or can be prepared for example as described in the review article by N. Miyaura and A. Suzuki, *Chem. Rev.* 1995, 95, 2457. Thus, boronates can be prepared by reacting the corresponding bromo-compound with an alkyl lithium such as butyl lithium and then reacting with a borate ester. The resulting boronate ester derivative can, if desired, be hydrolysed to give the corresponding boronic acid.

The Suzuki coupling reaction gives rise to an N-oxide compound corresponding to formula (1) wherein $X^1$ is $N^+(O^-)$ and $X^2$ is N. The N-oxide may be reduced to the corresponding non N-oxide corresponding to formula (1) wherein $X^1$ is N and $X^2$ is N using a reducing agent such as sodium dithionite ($Na_{22}O_4$). The reduction may be carried out in an aqueous solvent such as aqueous ethanol, usually with heating, for example at reflux.

Scheme 2

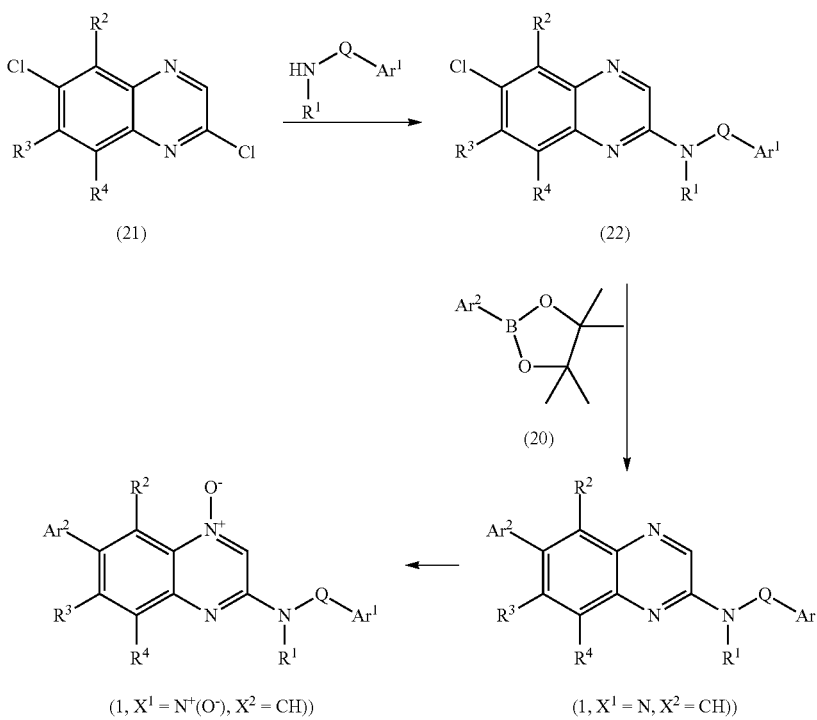

Compounds of the formula (1), and their N-oxides, may be prepared by the sequence of reactions shown in Scheme 2 above.

The starting material for Scheme 2 is the 2,6-dichoroquinoxaline (21) which is commercially available (when $R^2$, $R^3$ and $R^4$ are all hydrogen) or can be made by methods well known to the skilled chemist or methods analogous thereto.

The first step in the reaction sequence comprises the displacement of the 2-chlorine atom of the 2,6-dichoroquinoxaline (21) by $Ar^1$-Q-$NR^2$ by reaction with an amine compound of the formula $Ar^1$-Q-$NR^2$H to give the 6-chloroquinoxaline (22). The displacement reaction may be carried out in a polar solvent such as DMF or DMSO, typically at room temperature.

The 6-chloroquinoxaline (22) is then subjected to a Suzuki coupling reaction with a boronate or boronic acid derivative of the formula $Ar^2$-Bor under the conditions described above for Scheme 1, to give a compound of the formula (1) wherein $X^1$ is N and $X^2$ is CH. In Scheme 2, $Ar^2$-Bor is exemplified by the boronic acid pinacol ester (20).

The compound of formula (1) can then, if desired, be oxidised to the N-oxide by reaction with an oxidising agent such as hydrogen peroxide (for example $H_2O_2$ in acetic acid) to give the corresponding N-oxide of formula (1) wherein $X^1$ is $N^+O^-$ and $X^2$ is CH.

Further examples of synthetic routes to the compounds of formula (1) are described in the Examples section below.

Once formed, one compound of the formula (1) or a protected derivative thereof, can be converted into another compound of the formula (1) by methods well known to the skilled person. Examples of synthetic procedures for converting one functional group into another functional group are set out in standard texts such as *Advanced Organic Chemistry, by Jerry March,* 4th edition, 119, Wiley Interscience, New York; *Fiesers' Reagents for Organic Synthesis,* Volumes 1-17, John Wiley, edited by Mary Fieser (ISBN: 0-471-58283-2); and *Organic Syntheses,* Volumes 1-8, John Wiley, edited by Jeremiah P. Freeman (ISBN: 0-471-31192-8)).

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Green and P. Wuts; $3^{rd}$ Edition; John Wiley and Sons, 1999).

Compounds made by the foregoing methods may be isolated and purified by any of a variety of methods well known to those skilled in the art and examples of such methods include recrystallisation and chromatographic techniques such as column chromatography (e.g. flash chromatography) and preparative HPLC.

Pharmaceutical Formulations

While it is possible for the active compound to be administered alone, it is preferable to present it as a pharmaceutical composition (e.g. formulation).

Accordingly, in another embodiment (Embodiment 4.1) of the invention, there is provided a compound for use as defined in any one of Embodiments 1.0 to 1.55 or a compound according to Embodiment 1.56 or Embodiment 1.57 wherein the compound is in the form of a pharmaceutical composition comprising at least one said compound together with a pharmaceutically acceptable excipient.

The pharmaceutically acceptable excipient can be, for example, a carrier (e.g. a solid, liquid or semi-solid carrier), a diluent or bulking agent, a granulating agent, coating agent, binding agent, disintegrant, lubricating agent, preservative, antioxidant, buffering agent, suspending agent, thickening agent, flavouring agent, sweetener, taste masking agent or any other excipient conventionally used in pharmaceutical compositions. Examples of excipients for various types of pharmaceutical compositions are set out in more detail below.

The pharmaceutical compositions can be in any form suitable for oral, parenteral, topical, intranasal, ophthalmic, optic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the use of a suitable infusion pump.

Pharmaceutical formulations adapted for parenteral administration include aqueous and non-aqueous sterile injection solutions which may contain anti-oxidants, buffers, bacteriostats, co-solvents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, providing the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

A drug molecule that is ionizable can be solubilized to the desired concentration by pH adjustment if the drug's $pK_a$ is sufficiently away from the formulation pH value. The acceptable range is pH 2-12 for intravenous and intramuscular administration, but subcutaneously the range is pH 2.7-9.0. The solution pH is controlled by either the salt form of the drug, strong acids/bases such as hydrochloric acid or sodium hydroxide, or by solutions of buffers which include but are not limited to buffering solutions formed from glycine, citrate, acetate, maleate, succinate, histidine, phosphate, tris(hydroxymethyl)-aminomethane (TRIS), or carbonate.

The combination of an aqueous solution and a water-soluble organic solvent/surfactant (i.e., a cosolvent) is often used in injectable formulations. The water-soluble organic solvents and surfactants used in injectable formulations include but are not limited to propylene glycol, ethanol, polyethylene glycol 300, polyethylene glycol 400, glycerin, dimethylacetamide (DMA), N-methyl-2-pyrrolidone (NMP; Pharmasolve), dimethylsulphoxide (DMSO), Solutol HS 15, Cremophor EL, Cremophor RH 60, and polysorbate 80. Such formulations can usually be, but are not always, diluted prior to injection.

Propylene glycol, PEG 300, ethanol, Cremophor EL, Cremophor RH 60, and polysorbate 80 are the entirely organic water-miscible solvents and surfactants used in commercially available injectable formulations and can be used in combinations with each other. The resulting organic formulations are usually diluted at least 2-fold prior to IV bolus or IV infusion.

Alternatively, increased water solubility can be achieved through molecular complexation with cyclodextrins.

The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use.

The pharmaceutical formulation can be prepared by lyophilising a compound as defined in any one Embodiments 1.0 to 1.57. Lyophilisation refers to the procedure of freeze-drying a composition. Freeze-drying and lyophilisation are therefore used herein as synonyms. A typical process is to solubilise the compound and the resulting formulation is clarified, sterile filtered and aseptically transferred to containers appropriate for lyophilisation (e.g. vials). In the case of vials, they are partially stoppered with lyo-stoppers. The formulation can be cooled to freezing and subjected to lyophilisation under standard conditions and then hermetically capped forming a stable, dry lyophile formulation. The composition will typically have a low residual water content, e.g. less than 5% e.g. less than 1% by weight based on weight of the lyophile.

The lyophilisation formulation may contain other excipients for example, thickening agents, dispersing agents, buffers, antioxidants, preservatives, and tonicity adjusters. Typical buffers include phosphate, acetate, citrate and glycine. Examples of antioxidants include ascorbic acid, sodium bisulphite, sodium metabisulphite, monothioglycerol, thiourea, butylated hydroxytoluene, butylated hydroxyl anisole, and ethylenediaminetetraacetic acid salts. Preservatives may include benzoic acid and its salts, sorbic acid and its salts, alkyl esters of para-hydroxybenzoic acid, phenol, chlorobutanol, benzyl alcohol, thimerosal, benzalkonium chloride and cetylpyridinium chloride. The buffers mentioned previously, as well as dextrose and sodium chloride, can be used for tonicity adjustment if necessary.

Bulking agents are generally used in lyophilisation technology for facilitating the process and/or providing bulk and/or mechanical integrity to the lyophilized cake. Bulking agent means a freely water soluble, solid particulate diluent that when co-lyophilised with the compound or salt compound provides a physically stable lyophilized cake, a more optimal freeze-drying process and rapid and complete reconstitution. The bulking agent may also be utilised to make the solution isotonic.

The water-soluble bulking agent can be any of the pharmaceutically acceptable inert solid materials typically used for lyophilisation. Such bulking agents include, for example, sugars such as glucose, maltose, sucrose, and lactose; polyalcohols such as sorbitol or mannitol; amino acids such as glycine; polymers such as polyvinylpyrrolidine; and polysaccharides such as dextran.

The ratio of the weight of the bulking agent to the weight of active compound is typically within the range from about 1 to about 5, for example of about 1 to about 3, e.g. in the range of about 1 to 2.

Alternatively, they can be provided in a solution form which may be concentrated and sealed in a suitable vial. Sterilisation of dosage forms may be via filtration or by autoclaving of the vials and their contents at appropriate stages of the formulation process. The supplied formulation may require further dilution or preparation before delivery for example dilution into suitable sterile infusion packs.

Extemporaneous injection solutions and suspensions may be prepared from sterile powders, granules and tablets.

In one preferred embodiment of the invention, the pharmaceutical composition is in a form suitable for i.v. administration, for example by injection or infusion.

In another preferred embodiment, the pharmaceutical composition is in a form suitable for sub-cutaneous (s.c.) administration.

Pharmaceutical dosage forms suitable for oral administration include tablets, capsules, caplets, pills, lozenges, syrups, solutions, powders, granules, elixirs and suspensions, sublingual tablets, wafers or patches and buccal patches.

Pharmaceutical compositions containing compounds of the formula (I) can be formulated in accordance with known techniques, see for example, Remington's Pharmaceutical Sciences, Mack Publishing Company, Easton, Pa., USA.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum or duodenum.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art.

The compound as defined in any one of Embodiments 1.0 to 1.57, or a prodrug thereof, may be formulated with a carrier and administered in the form of nanoparticles. Nanoparticles offer the possibility of direct penetration into the cell. Nanoparticle drug delivery systems are described in "Nanoparticle Technology for Drug Delivery", edited by Ram B Gupta and Uday B. Kompella, Informa Healthcare, ISBN 9781574448573, published 13 Mar. 2006. Nanoparticles for drug delivery are also described in J. Control. Release, 2003, 91 (1-2), 167-172, and in Sinha et al., Mol. Cancer Ther. August 1, (2006) 5, 1909.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use include ointments, creams, sprays, patches, gels, liquid drops and inserts (for example intraocular inserts). Such compositions can be formulated in accordance with known methods.

Compositions for parenteral administration are typically presented as sterile aqueous or oily solutions or fine suspensions, or may be provided in finely divided sterile powder form for making up extemporaneously with sterile water for injection.

Examples of formulations for rectal or intra-vaginal administration include pessaries and suppositories which may be, for example, formed from a shaped moldable or waxy material containing the active compound.

Compositions for administration by inhalation may take the form of inhalable powder compositions or liquid or powder sprays, and can be administered in standard form using powder inhaler devices or aerosol dispensing devices. Such devices are well known. For administration by inhalation, the powdered formulations typically comprise the active compound together with an inert solid powdered diluent such as lactose.

The compounds for use in accordance with the invention will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within this range, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 miligrams to 1 gram, of active compound.

The active compound will be administered to a patient in need thereof (for example a human or animal patient) in an amount sufficient to achieve the desired therapeutic effect.

Methods of Treatment

It is envisaged that the compounds defined in any one of Embodiments 1.0 to 1.57 will be useful either as sole therapeutic agents in the treatment of brain disorders or will be used in combination therapy with other therapeutic agents or therapeutic treatments. For example, where the brain disorder to be treated is a cancer, the compounds of the invention can be used in combination therapy with chemotherapeutic agents or radiation therapy in the prophylaxis or treatment of a range of proliferative disease states or conditions. Examples of such disease states and conditions are set out above.

Particular examples of chemotherapeutic agents that may be co-administered with the compounds of any of Embodiments 1.0 to 1.57 include:
Topoisomerase I inhibitors
Antimetabolites
Tubulin targeting agents
DNA binder and topoisomerase II inhibitors
EGFR inhibitors and other PI3K pathway inhibitors
mTOR inhibitors (e.g. Everolimus)
Akt inhibitors
Alkylating Agents (e.g. temozolomide)
Monoclonal Antibodies. E.g. antibodies targeting CTLA-4, PD-1, PD-L1, CD52 or CD20.
Anti-Hormones
Signal Transduction Inhibitors
Proteasome Inhibitors
DNA methyl transferases
Cytokines and retinoids
Hypoxia triggered DNA damaging agents (e.g. Tirapazamine)
B-Raf inhibitors
VEGFR inhibitors
IGFR-1 inhibitors
ERK inhibitors
Inhibitors of the Hedgehog signaling pathway Further examples of chemotherapeutic agents that may be co-administered with a compound as defined in any one Embodiments 1.0 to 1.57:
Torc 1 inhibitors
Aromatase inhibitors
Anti Her2 antibodies, e.g. Herceptin (see for example http://www.wipo.int/pctdb/en/wo-.jsp?wo=2007056118)
HER2 small molecule inhibitors (e.g. lapatinib)
Inhibitors of angiogenesis
HDAC inhibitors
PI3K pathway inhibitors (e.g. PI3K, PDK1)
MEK inhibitors
EGFR inhibitors (e.g. Gefitinib—refer to: Everolimus restores gefitinib sensitivity in resistant non-small cell lung cancer cell lines, Biochemical Pharmacology 78 2009 460-468)
Bcr-Abl tyrosine-kinase inhibitors (e.g. imatinib)
CDK4/6 inhibitors e.g. Ibrance
Taxanes (e.g. paclitaxel, docetaxel, cabazitaxel)
Platinum agents (e.g. cisplatin, carboplatin, oxaliplatin)
Anthracyclines (e.g. Doxorubicin)
Inhibitors of Bcl-2 family proteins e.g. ABT263 (navitoclax), a Bcl-2/Bcl-extra large (Bcl-xL) inhibitor One particular combination comprises a compound according to any one of Embodiments 1.0 to 1.57 together with an EGFR inhibitor such as Gefitinib.

The compounds may also be administered in conjunction with radiotherapy.

Fragile X syndrome usually manifests first in childhood. A delay in speech is common and is often the first symptom that brings the child to medical attention (around the age of two or three). Accordingly, the invention provides a compound according to any one of Embodiments 1.0 to 1.57 for use in the treatment of Fragile X syndrome in a patient under the age of 20, for example under the age of 15, or under the age of 12, or under the age of 10, preferably below the age of 8, and even more preferably under the age of 5.

In another embodiment of the invention there is provided a method for the treatment of Fragile X syndrome which method comprises administering a patient in need thereof a compound as defined in any one of Embodiments 1.0 to 1.57, wherein the patient is under the age of 20, for example under the age of 15, or under the age of 12, or under the age of 10, preferably below the age of 8, and even more preferably under the age of 5.

In another embodiment there is provided the use of a compound as defined in any one of Embodiments 1.0 to 1.57 for the manufacture of a medicament for the treatment or prophylaxis of Fragile X syndrome in a patient under the age of 20, for example under the age of 15, or under the age of 12, or under the age of 10, preferably below the age of 8, and, even more preferably under the age of 5.

The compounds may be administered over a prolonged term to maintain beneficial therapeutic effects or may be administered for a short period only. Alternatively, they may be administered in a pulsatile or continuous manner.

The compounds of the invention will be administered in an effective amount, i.e. an amount which is effective to bring about the desired therapeutic effect. For example, the "effective amount" can be a quantity of compound which, when administered to a subject suffering from cancer, slows tumour growth, ameliorates the symptoms of the disease and/or increases longevity.

The amount of P70S6 inhibitor compound of the invention administered to the subject will depend on the type and severity of the disease or condition and on the characteristics of the subject, such as general health, age, sex, body weight and tolerance to drugs. The skilled person will be able to determine appropriate dosages depending on these and other factors.

The compounds are generally administered to a subject in need of such administration, for example a human or animal patient, preferably a human.

A typical daily dose of the compound of formula (1) can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound can be administered on a daily basis or on a repeat basis every 2, or 3, or 4, or 5, or 6, or 7, or 10 or 14, or 21, or 28 days for example.

In one particular dosing schedule, a patient will be given an infusion of a compound for periods of one hour daily for up to ten days in particular up to five days for one week, and the treatment repeated at a desired interval such as two to four weeks, in particular every three weeks.

More particularly, a patient may be given an infusion of a compound for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

In a further particular dosing schedule, a patient is given a continuous infusion for a period of 12 hours to 5 days, an in particular a continuous infusion of 24 hours to 72 hours.

Ultimately, however, the quantity of compound administered and the type of composition used will be commensurate with the nature of the disease or physiological condition being treated and will be at the discretion of the physician.

Methods of Diagnosis

Prior to administration of a compound as defined in any one Embodiments 1.0 to 1.57, a patient may be screened to determine whether a disease or condition from which the patient is or may be suffering is one which would be susceptible to treatment with a compound having activity against p70S6 kinase.

For example, a biological sample taken from a patient may be analysed to determine whether a condition or disease, such as cancer, that the patient is or may be suffering from is one which is characterised by a genetic abnormality or abnormal protein expression which leads to up-regulation of p70S6 kinase or to sensitisation of a pathway to normal p70S6 kinase activity or to over-expression of phosphorylated p70S6 kinase. The term up-regulation includes elevated expression or over-expression, including gene amplification (i.e. multiple gene copies) and increased expression by a transcriptional effect, and hyperactivity and activation, including activation by mutations. Thus, the patient may be subjected to a diagnostic test to detect a marker characteristic of up-regulation of p70S6 kinase. The term diagnosis includes screening. By marker we include genetic markers including, for example, the measurement of DNA composition to identify mutations of p70S6. The term marker also includes markers which are characteristic of up-regulation of p70S6, including enzyme activity, enzyme levels, enzyme state (e.g. phosphorylated or not) and mRNA levels of the aforementioned proteins.

Tumours with upregulation of p70S6 kinase may be particularly sensitive to p70S6 inhibitors. Tumours may preferentially be screened for upregulation of p70S6. Thus, the patient may be subjected to a diagnostic test to detect a marker characteristic of up-regulation of p70S6. The diagnostic tests are typically conducted on a biological sample selected from tumour biopsy samples, blood samples (isolation and enrichment of shed tumour cells), stool biopsies, sputum, chromosome analysis, pleural fluid, peritoneal fluid, Methods of identification and analysis of mutations and up-regulation of proteins are known to a person skilled in the art. Screening methods could include, but are not limited to, standard methods such as reverse-transcriptase polymerase chain reaction (RT-PCR) or in-situ hybridisation.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. Current Protocols in Molecular Biology, 2004, John Wiley & Sons Inc., or Innis, M. A. et-al., eds. PCR Protocols: a guide to methods and applications, 1990, Academic Press, San Diego. Reactions and manipulations involving nucleic acid techniques are also described in Sambrook et al., 2001, $3^{rd}$ Ed, Molecular Cloning: A Laboratory Manual, Cold Spring Harbor Laboratory Press. Alternatively, a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference.

An example of an in-situ hybridisation technique for assessing mRNA expression would be fluorescence in-situ hybridisation (FISH) (see Angerer, 1987 Meth. Enzymol., 152: 649)

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labeled, for example, with radio-isotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. Current Protocols in Molecular Biology, 2004, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Alternatively, the protein products expressed from the mRNAs may be assayed by immunohistochemistry of tumour samples, solid phase immunoassay with microtiter plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of up-regulation of p70S6 kinase could be applicable in the present case.

Accordingly, in another embodiment of the invention (Embodiment 5.1), there is provided a method for the diagnosis and treatment of a brain disorder mediated by p70S6 kinase which method comprises (i) screening a patient to determine whether a brain disorder from which the patient is or may be suffering is one which would be susceptible to treatment with a compound having activity against p70S6 kinase; and (ii) where it is indicated that the brain disorder from which the patient is thus susceptible, thereafter administering to the patient a compound as defined in any one of Embodiments 1.0 to 1.57.

In another embodiment (Embodiment 5.2), there is provided the use of a compound as defined in any one of Embodiments 1.0 to 1.57 for the manufacture of a medicament for the treatment or prophylaxis of a brain disorder in a patient who has been screened and has been determined as suffering from, or being at risk of suffering from, a brain disorder which would be susceptible to treatment with a compound having activity against p70S6.

In a further embodiment (Embodiment 5.3), there is provided a compound as defined in any one of Embodiments 1.0 to 1.57 for use in the treatment or prophylaxis of a brain disorder in a patient who has been screened and has been determined as suffering from, or being at risk of suffering from, a brain disorder which would be susceptible to treatment with a compound having activity against p70S6.

In another embodiment of the invention (Embodiment 5.4), there is provided a method for the diagnosis and treatment of a brain disorder characterised by up-regulation of p70S6 kinase or the presence of a mutated form of p70S6, which method comprises (i) screening a patient to determine whether a disease or condition from which the patient is or may be suffering is one which would be susceptible to treatment with a compound having activity against p70S6 kinase; and (ii) where it is indicated that the disease or condition from which the patient is thus susceptible, thereafter administering to the patient a compound as defined in any one of Embodiments 1.0 to 1.57.

In another embodiment of the invention (Embodiment 5.5), there is provided a method for the diagnosis and treatment of a disease, condition or disorder as defined in any one of Embodiments 2.1 to 2.43, which method comprises (i) screening a patient to determine whether a disease, condition or disorder from which the patient is or may be suffering is one which would be susceptible to treatment with a compound having activity against p70S6 kinase; and (ii) where it is indicated that the disease, condition or disorder from which the patient is thus susceptible, thereafter administering to the patient a compound as defined in any one of Embodiments 1.0 to 1.57.

In another embodiment (Embodiment 5.6), there is provided the use of a compound as defined in any one of Embodiments 1.0 to 1.57 for the manufacture of a medicament for the treatment or prophylaxis of a disease, condition of disorder as defined in any one of Embodiments 2.1 to 2.43 in a patient who has been screened and has been determined as suffering from, or being at risk of suffering from, a said disease, condition or disorder which would be susceptible to treatment with a compound having activity against p70S6.

In a further embodiment (Embodiment 5.7), there is provided a compound as defined in any one of Embodiments 1.0 to 1.57 for use in the treatment or prophylaxis of a disease or brain disorder in a patient who has been screened and has been determined as suffering from, or being at risk of suffering from, a disease, condition or disorder as defined in any one of Embodiments 2.1 to 2.43 in a patient who has been screened and has been determined as suffering from, or being at risk of suffering from a said disease, condition or disorder which would be susceptible to treatment with a compound having activity against p70S6.

Triple-negative breast cancers are characterised in that the cancer does not express the genes for estrogen receptor (ER), progesterone receptor (PR) or HER2. The presence of ER and PR can be determined by standard immuno-histochemical staining methods (see for example, Narod et al, Triple-Negative Breast Cancer: Clinical Features and Patterns of Recurrence, Clin Cancer Res Aug. 1, 2007 13; 4429). Alternatively, it is possible to assess gene expression of these proteins by methods such as Quantitative real-time polymerase chain reaction (QRT-PCR) with commercially available PCR assays (see Jozefczuk et al, Quantitative real-time PCR-based analysis of gene expression, Methods Enzymol. 2011;500:99-109).

Overexpression of the HER2 protein can be evaluated using the CB11 monoclonal antibody in representative paraffin sections of each tumour using the peroxidase-antiperoxidase technique for immunohistochemical assay. A tumour is defined as exhibiting HER2 positivity when strong complete membrane staining is observed in at least 10% of tumour cells (Narod et al, Clin Cancer Res Aug. 1, 2007 13; 4429).

Accordingly, in another embodiment of the invention (Embodiment 5.8), there is provided a method for the diagnosis and treatment of a cancer as defined in any one of Embodiments 2.1 to 2.9, which method comprises (i) screening a patient to determine whether a cancer from which the patient is or may be suffering is one which does not express estrogen receptor, progesterone receptor and/or HER2; and (ii) where it is indicated that the cancer which the patient is thus susceptible to, thereafter administering to the patient a compound as defined in any one of Embodiments 1.0 to 1.57.

In another embodiment (Embodiment 5.9), there is provided the use of a compound as defined in any one of Embodiments 1.0 to 1.57 for the manufacture of a medicament for the treatment or prophylaxis of a cancer as defined in any one of Embodiments 2.1 to 2.9 in a patient who has been screened and has been determined as suffering from, or being at risk of suffering, from a cancer which does not express estrogen receptor, progesterone receptor and/or HER2.

In a further embodiment (Embodiment 5.10), there is provided a compound as defined in any one of Embodiments 1.0 to 1.57 for use in the treatment or prophylaxis of a cancer as defined in any one of Embodiments 2.1 to 2.9 in a patient who has been screened and has been determined as suffering from, or being at risk of suffering, from a cancer which does not express estrogen receptor, progesterone receptor and/or HER2.

Fragile X syndrome occurs as a result of a mutation of the fragile X mental retardation 1 gene (FMR1). In individuals affected by FXS, the FMR1 gene contains over 45, more commonly over 55 and in some cases over 200 repeats of the CGG codon compared to between 5 and 44 times, more commonly either 29 or 30 times, in unaffected individuals.

This mutation results in a failure to express fragile X mental retardation protein FMRP leading to excessive production of an array of proteins normally controlled by FMRP. As FXS is a genetic disease, diagnosis of FXS can be readily accomplished by running a genetic test from a blood or skin sample of the patient in question. FXS patients will not express or have much lower FMR1 mRNA levels than unaffected individuals. The levels of FMR1 mRNA levels may be quantified using real-time PCR, assays for which are commercially available. In addition, the size of the CGG repeat can be determined by isolating genomic DNA by salting out followed by PCR. See, for example, Kumari et al. (HUMAN MUTATION, Vol. 35, No. 12, 1485-1494, 2014) for laboratory methods to obtain this data. Thus, biomarkers that enable FXS to be identified in a patient include FMR1 mRNA levels and the presence of oversized CGG repeats in a patient's genomic DNA.

Accordingly, in another embodiment of the invention (Embodiment 5.11), there is provided a method for the diagnosis and treatment of Fragile X syndrome, which method comprises (i) screening a patient for one or more biomarkers indicative of Fragile X syndrome; and (ii) where such a biomarker is detected, thereafter administering to the patient a compound as defined in any one of Embodiments 1.0 to 1.57.

In another embodiment (Embodiment 5.12), there is provided the use of a compound as defined in any one of Embodiments 1.0 to 1.57 for the manufacture of a medicament for the treatment or prophylaxis of Fragile X syndrome in a patient who has been screened for and found to harbour one or more biomarkers indicative of Fragile X syndrome.

In a further embodiment (Embodiment 5.13), there is provided a compound as defined in any one of Embodiments 1.0 to 1.57 for use in the treatment or prophylaxis of Fragile X syndrome in a patient who has been screened for and found to harbour one or more biomarkers indicative of Fragile X syndrome. In another embodiment of the invention (Embodiment 5.14), there is provided a method for the diagnosis and treatment of Fragile X syndrome, which method comprises (i) screening a patient to determine whether they have levels of FMR1 mRNA indicative of Fragile X syndrome; and (ii) where it is indicated that they do have such levels of FMR1 mRNA, thereafter administering to the patient a compound as defined in any one of Embodiments 1.0 to 1.57.

In another embodiment (Embodiment 5.15), there is provided the use of a compound as defined in any one of Embodiments 1.0 to 1.57 for the manufacture of a medicament for the treatment or prophylaxis of Fragile X syndrome in a patient who has been screened and has been determined as having levels of FMR1 mRNA indicative of Fragile X syndrome.

In a further embodiment (Embodiment 5.16), there is provided a compound as defined in any one of Embodiments 1.0 to 1.57 for use in the treatment or prophylaxis of Fragile X syndrome in a patient who has been screened and has been determined as having levels of FMR1 mRNA indicative of Fragile X syndrome.

EXAMPLES

Figure 1:
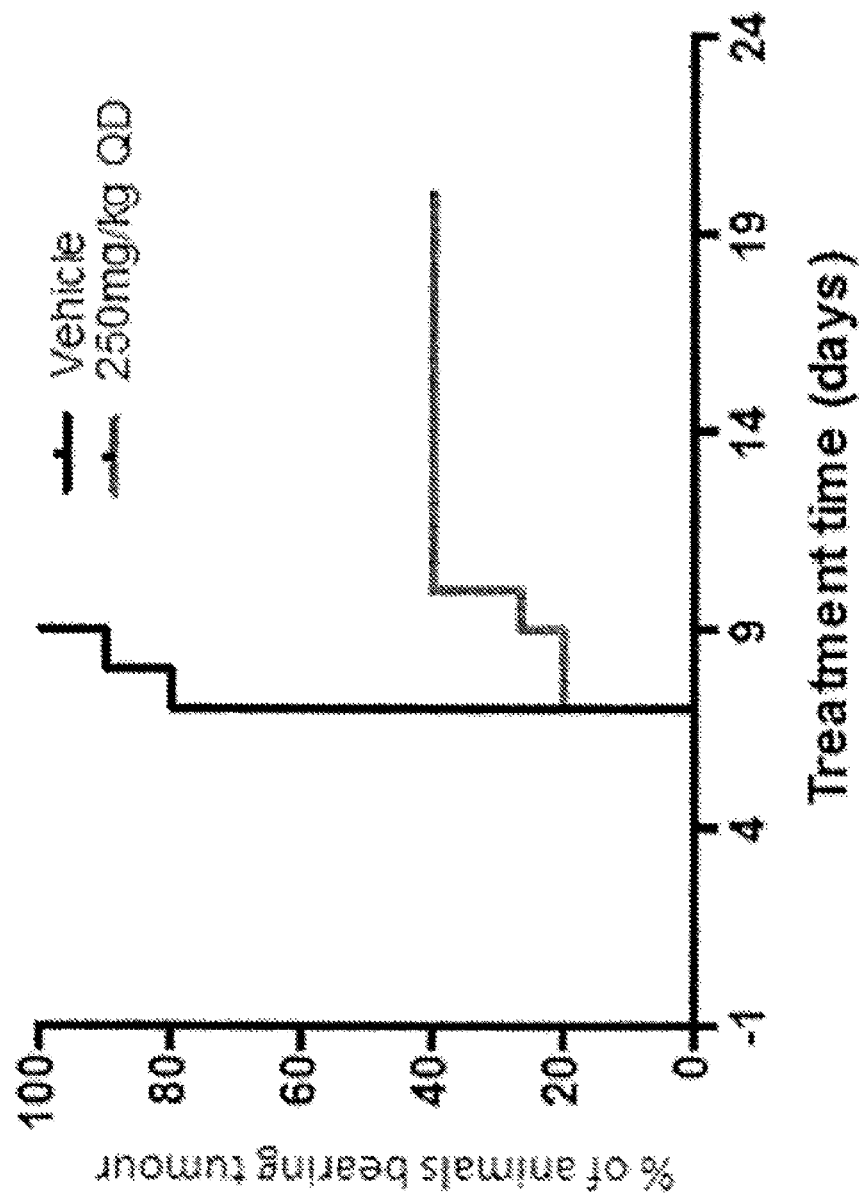
FIG. 1 is a plot of the percentage of MDA-MB-231 tumour-bearing test animals (nude athymic mice) versus time following treatment with either the compound of Example 15 of the present invention or a vehicle control.

The compounds shown in Table 1 below have been made and tested.

TABLE 1

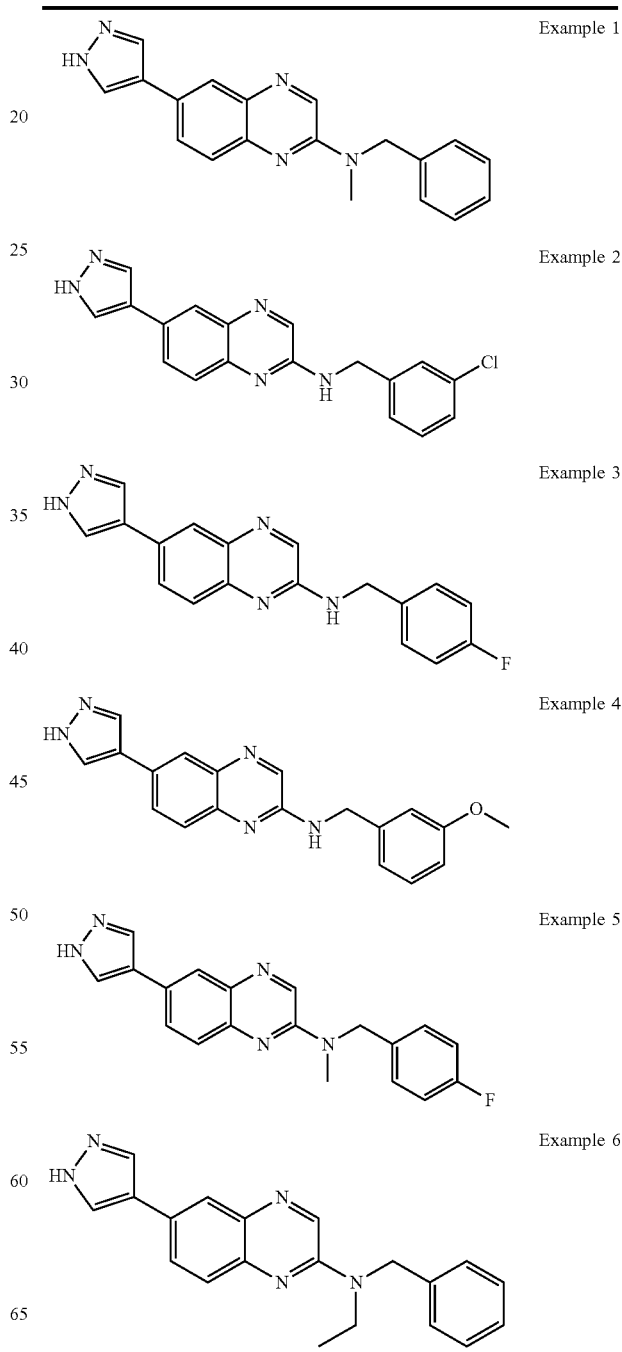

TABLE 1-continued

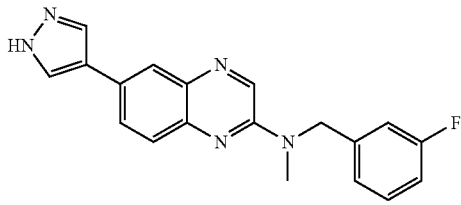 [SMILES: CN(Cc1cccc(F)c1)c1cnc2cc(-c3cn[nH]c3)ccc2n1]
Example 7

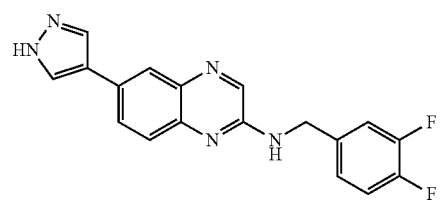 [SMILES: Fc1ccc(CNc2cnc3cc(-c4cn[nH]c4)ccc3n2)cc1F]
Example 8

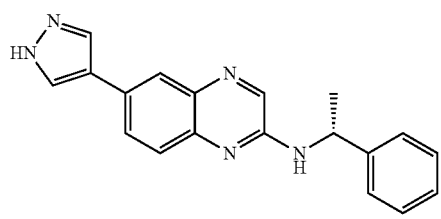 [SMILES: C[C@@H](Nc1cnc2cc(-c3cn[nH]c3)ccc2n1)c1ccccc1]
Example 9

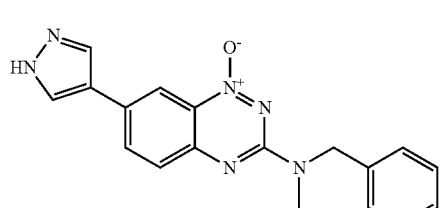
Example 10

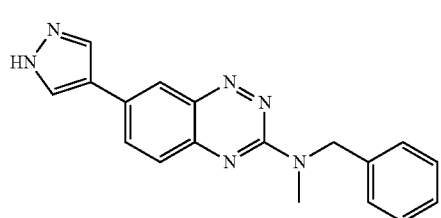
Example 11

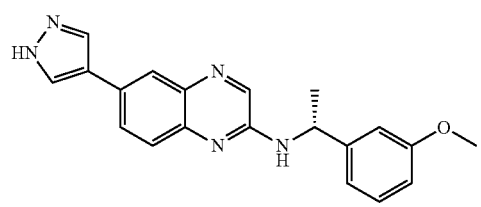 [SMILES: COc1cccc([C@@H](C)Nc2cnc3cc(-c4cn[nH]c4)ccc3n2)c1]
Example 12

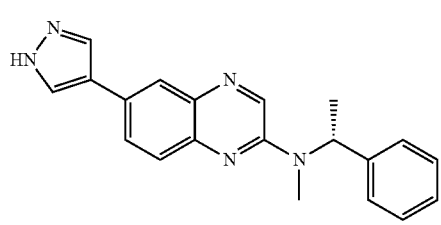 [SMILES: C[C@H](c1ccccc1)N(C)c1cnc2cc(-c3cn[nH]c3)ccc2n1]
Example 13

TABLE 1-continued

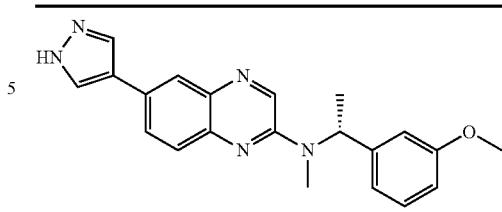
Example 14

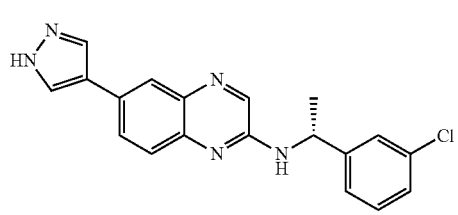 [SMILES: C[C@@H](Nc1cnc2cc(-c3cn[nH]c3)ccc2n1)c1cccc(Cl)c1]
Example 15

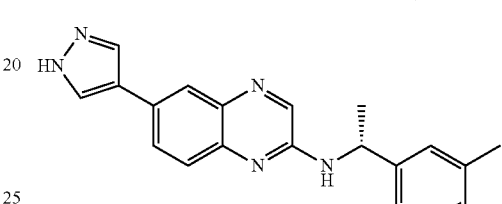
Example 16

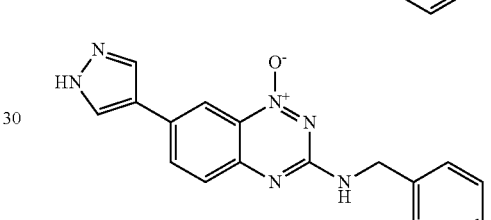
Example 17

Examples 1 to 17

The compounds of Examples 1 to 17 correspond to the compounds of Examples 2, 9, 11, 18, 21, 26, 28, 32, 33, 34, 35, 50, 51, 53, 55, 58 and 61 in our earlier International patent application WO2010/136755 and were made according to the methods described in the said examples.

Examples 18 and 19

Analytical Data
$^1$H NMR spectra were recorded on a Bruker 400 machine.
LCMS Methods:
LCMS analysis was carried using the following method(s):
LCMS Method A
LC-MS was carried out using a WATERS-2690 device with Qda mass detector using Positive/negative electrospray ionisation. Sample solution injection volume: 10 µl. Temperature: 25° C. Analytical column: X-Bridge C18 (100× 4.6)mm, 5 micron. Column flow was 1.0 mL/min. Solvent system: using (A) 0.1% formic acid (FA) in HPLC grade water and (B) 100% HPLC grade methanol according to the following gradient:

| Time (min) | % A | % B |
|---|---|---|
| 0.01 | 90 | 10 |
| 3.00 | 10 | 90 |

-continued

| Time (min) | % A | % B |
|---|---|---|
| 6.00 | 0 | 100 |
| 7.00 | 0 | 100 |
| 7.01 | 90 | 10 |
| 10.00 | 90 | 10 |

Chiral HPLC Methods:

Chiral HPLC analysis was carried out using the following method(s):

Chiral HPLC Method A

Chiral HPLC was carried out using an Agilent 1200 series HPLC device. Sample solution injection volume: 15 μl. Column oven temperature was 35° C. Analytical column: Chiral pak IB (250×4.6) mm, 5 micron. Flow rate: 1.0 ml/min. Solvent system: (A) 0.1% diethylamine in n-heptane; and (B) 0.1% diethylamine in ethanol according to the following gradient:

| Time (min) | % A | % B |
|---|---|---|
| 0 | 90 | 10 |
| 5 | 90 | 10 |
| 10 | 70 | 30 |
| 15 | 70 | 30 |

| Time (min) | % A | % B |
|---|---|---|
| 25 | 40 | 60 |
| 30 | 15 | 85 |
| 35 | 15 | 85 |
| 35.01 | 90 | 10 |
| 40 | 90 | 10 |

Example 18

1-oxido-N-[(1R)-1-phenylethyl]-7-(1H-pyrazol-4-yl)-1,2,4-benzotriazin-1-ium-3-amine hydrochloride

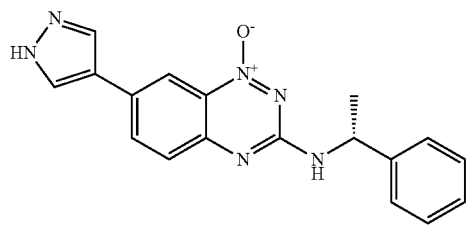

Synthetic Scheme A

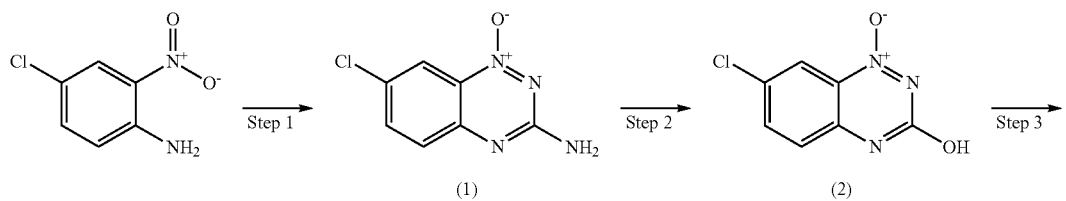

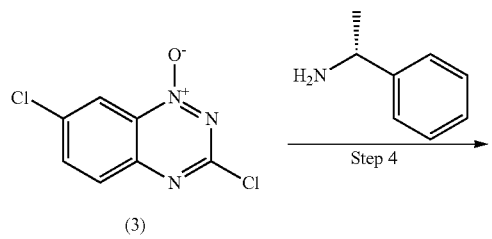

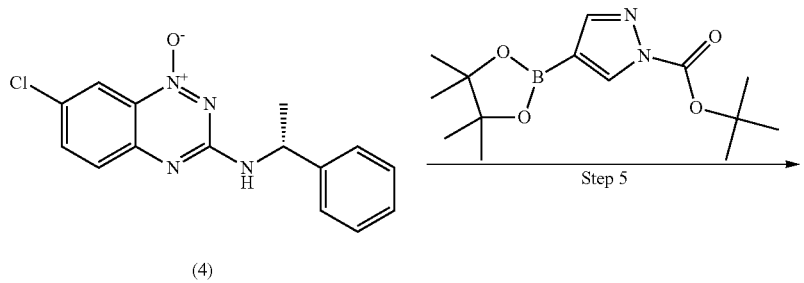

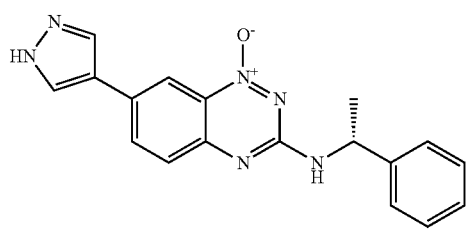 [SMILES: C[C@@H](Nc1nc2ccc(-c3cn[nH]c3)cc2[n+]([O-])n1)c1ccccc1]

(5)

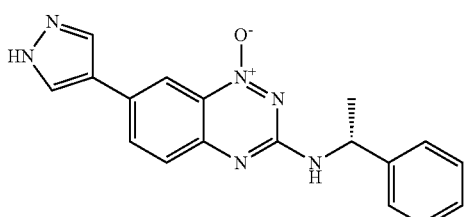

(7A)

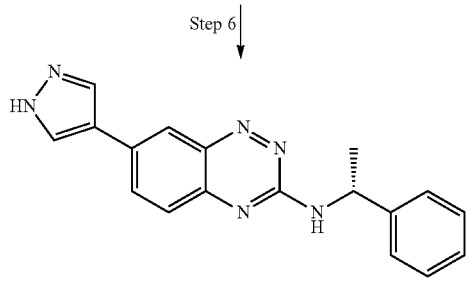

(6)

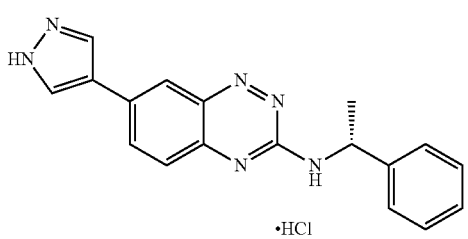

(7B)

Step 1:
7-chloro-1-oxido-1,2,4-benzotriazin-1-ium-3-amine

A mixture of 4-chloro-2-nitroaniline (10.0 g, 0.058 mol) and cyanamide (16.0 g, 0.38 mol) was slowly heated to 100° C. and then cooled to 50° C. To it was slowly added conc. HCl (20 mL) and the mixture was heated at 100° C. for 3 h. The reaction mixture was then cooled to room temperature and to it was added 50% w/v aqueous NaOH solution (40 mL). The reaction mixture was then heated at 100° C. for 1 h. The reaction was monitored on thin layer chromatography (TLC) (using ethyl acetate: hexane, 5:5 as mobile phase) which confirmed that the reaction had gone to completion. The reaction mixture was poured into ice water and the resulting precipitates were filtered-off to afford crude Intermediate 1, which was further purified by trituration using diethyl ether to afford title product (9.7 g, 85%).

Step 2:
7-chloro-1-oxido-1,2,4-benzotriazin-1-ium-3-ol

To a solution of 7-chloro-1-oxido-1,2,4-benzotriazin-1-ium-3-amine (4.5 g, 0.023 mol) in trifluoroacetic acid (45 mL) at 0° C. was slowly added sodium nitrite (2.38 g, 0.035 mol). The resulting reaction mixture was stirred at room temperature for 3 h. The reaction was monitored on TLC (using chloroform: methanol, 9:1 as mobile phase) which confirmed that the reaction had gone to completion. The reaction mixture was poured into ice water and the resulting precipitates were filtered off in vacuo to afford crude solid product, which was further purified by trituration using diethyl ether to afford title product (3.1 g, 68%).

Step 3:
3,7-dichloro-1-oxido-1,2,4-benzotriazin-1-ium 7-chloro-1-oxido-1,2,4-benzotriazin-1-ium-3-ol (6.3 g, 0.032 mol) was dissolved in phosphorus oxychloride (70 mL) and the solution was heated at 100° C. for 16 h. The reaction was monitored on TLC (using hexane: ethyl acetate, 7:3 as mobile phase) which confirmed that the reaction had gone to completion. The reaction mixture was poured into ice water and the resulting precipitates were filtered off in vacuo to afford crude product, which was further purified by flash column chromatography on silica eluting with 4% ethyl acetate in hexane to afford title product (5.3 g, 77%).

Step 4: 7-chloro-1-oxido-N-[(1R))-1-phenylethyl]-1, 2,4-benzotriazin-1-ium-3-amine To a solution of 3,7-dichloro-1-oxido-1,2,4-benzotriazin-1-ium (5.3 g, 0.025 mol) in dimethylsulphoxide (DMSO) (10 mL) at room temperature was added (1R)-1-phenylethanamine (7.48 g, 0.062 mol). The reaction mixture was then stirred for 0.5 h at room temperature. The reaction was monitored on TLC (using hexane: ethyl acetate, 8:2 as mobile phase) which confirmed that the reaction had gone to completion. The reaction mixture was poured into ice-water and the resulting solid precipitate was filtered off in vacuo to afford crude product, which was used in the next step without further purification (7.1 g, 96%).

Step 5: 1-oxido-N-[(1R)-1-phenylethyl]-7-(1H-pyrazol-4-yl)-1,2,4-benzotriazin-1-ium-3-amine To a solution of 7-chloro-1-oxido-N-[(1R)-1-phenylethyl]-1,2,4-benzotriazin-1-ium-3-amine (0.3 g, 0.9997 mmol) in 1,2-dimethoxyethane (8.4 mL) was added tert-butyl 4-(4,4,5,5-tetramethyl-1,3,2-dioxaborolan-2-yl)pyrazole-1-carboxylate (0.368 g, 1.25 mmol), solid sodium carbonate (0.318 g, 3.0 mmol), ethanol (0.9 mL) and water (1.4 mL). The reaction mixture was degassed with nitrogen gas for 30 minutes followed by addition of Fu's catalyst (0.01 g, 0.0196 mmol). The resulting reaction mixture was stirred at 105° C. for 30 minutes in a microwave reactor. The reaction was monitored on TLC (using hexane: ethyl acetate, 5:5 as mobile phase) which confirmed that the reaction had gone to completion. The reaction mixture was poured into ice-water and the aqueous was extracted with ethyl acetate (3×150 mL). The organic layers were combined and then brine-washed, dried over sodium sulphate, filtered and then concentrated in vacuo to afford crude product. The crude was further purified by flash column chromatography on silica, eluting with 40% ethyl acetate in hexane to afford title product (0.18 g, 55%).

Step 7: 1-oxido-N-[(1R)-1-phenylethyl]-7-(1H-pyrazol-4-yl)-1,2,4-benzotriazin-1-ium-3-amine hydrochloride 1-oxido-N-[(1R)-1-phenylethyl]-7-(1H-pyrazol-4-yl)-1,2,4-benzotriazin-1-ium-3-amine (0.1 g, 0.301 mmol) was dissolved in ethyl acetate (5 mL) and to this solution was added a solution of 4N HCl in dioxane (1 mL) at 0° C. The reaction mixture was stirred at room temperature for 10 minutes. The reaction mixture was then concentrated in vacuo to afford product, which was further triturated in ethyl acetate to afford title product (0.065 g, 59%).

Example 19

N-[(1 R)-1-phenylethyl]-7-(1H-pyrazol-4-yl)-1,2,4-benzotriazin-3-amine hydrochloride

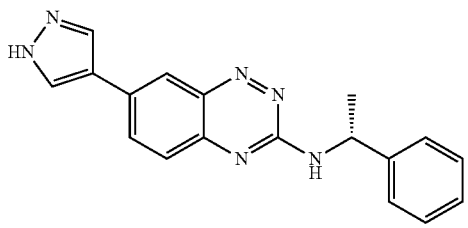 [SMILES: C[C@@H](Nc1nnc2cc(-c3cn[nH]c3)ccc2n1)c1ccccc1]

Using 1-oxido-N-[(1R)-1-phenylethyl]-7-(1H-pyrazol-4-yl)-1,2,4-benzotriazin-1-ium-3-amine from Example 18, step 5, the following was conducted:

Step 6: N-[(1R)-1-phenylethyl]-7-(1H-pyrazol-4-yl)-1,2,4-benzotriazin-3-amine 1-oxido-N-[(1R)-1-phenylethyl]-7-(1H-pyrazol-4-yl)-1,2,4-benzotriazin-1-ium-3-amine (0.25 g, 0.753 mmol) was dissolved in a mixture of ethanol (8 mL) and water (4 mL) and to this solution was added sodium dithionite (1.7 g, 9.76 mmol). The resulting reaction mixture was stirred at 80° C. for 1 h in a microwave reactor. The reaction was monitored on TLC (using chloroform: methanol, 92: 8 as mobile phase) which confirmed that the reaction had gone to completion. The reaction mixture was poured into ice-water and the resulting solid precipitate was filtered off in vacuo to afford the title product. The product was subjected to the same conditions as described in step 7 of example 66 to afford the title product as a HCl salt (0.095 g, 36%).

The characterizing data for the title compounds of Examples 18 and 19 are set out in the table below.

Analytical data table

| Example No. | Name | Synthetic scheme | $^1$H NMR | Chiral HPLC RT (min) | LC RT (min) | MS | Chiral HPLC method | LCMS method |
|---|---|---|---|---|---|---|---|---|
| 18 | 1-oxido-N-[(1R)-1-phenylethyl]-7-(1H-pyrazol-4-yl)-1,2,4-benzotriazin-1-ium-3-amine hydrochloride | A | 1H NMR (DMSO-d6) δ 9.90-9.31 (br s, 2H), 8.47-8.40 (br m, 1H), 8.295 (m, 3H), 8.09 (dd, 1H), 7.53 (d, 1H), 7.44 (d, 2H), 7.31 (t, 2H), 7.21 (t, 1H), 5.25-5.11 (br m, 1H), 1.50 (d, 3H) | 13.657 | 5.014 | 333.14 (MH+) | A | A |
| 19 | N-[(1R)-1-phenylethyl]-7-(1H-pyrazol-4-yl)-1,2,4-benzotriazin-3-amine hydrochloride | A | 1H NMR (DMSO-d6) 9.00-8.85 (br s, 1H), 8.41 (s, 1H), 8.29 (s, 2H), 8.12 (dd, 1H), 7.55-7.45 (m, 3H), 7.31 (t, 2H), 7.21 (t, 1H), 5.26-5.15 (br m, 1H), 1.55 (d, 3H) | 12.150 | 5.020 | 317.14 (MH+) | A | A |

Example 20

Biological Activity (a) Determination of p70S6 Inhibitory Activity

The ability of compounds of the invention to inhibit P70S6 kinase was determined using the protocol below.

Buffer Composition:

20 mM MOPS, 1 mM EDTA, 0.01% Brij-35, 5% Glycerol, 0.1% b-mercaptoethanol, 1 mg/mL BSA Method:

p70S6K (h)

In a final reaction volume of 25 μL, p70S6K (h) (5-10 mU) is incubated with 8 mM MOPS pH 7.0, 0.2 mM EDTA, 100 μM KKRNRTLTV, 10 mM Mg acetate and [γ-33P-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction mixture is then spotted onto a P30 filtermat and washed three times for 5 minutes in 75 mM phosphoric acid and once in methanol prior to drying and scintillation counting.

The IC$_{50}$ values obtained for the compounds tested are set out in the table below.

(b) Investigating the Mechanism of Action of p70S6K Inhibitors in MCF-7 Cells by pS6 ELISA The following assay provides IC$_{50}$ values for inhibition of P70S6K activity in a whole cell assay by determining effects on the phosphorylation of S6$^{Ser235/236}$ in MCF-7 cells by ELISA.

Protocol:

The following protocol was used:
1) MCF-7 cells were seeded in 96-well plates at a density of 7000 cells per well and allowed to adhere for 6 h in media containing 10% FBS.
2) The full serum media was replaced and cells incubated overnight in media containing 1% FBS, prior to addition of test compounds.
3) Test compounds were prepared from 10 mM DMSO stocks to give final concentration ranges as indicated on graphs. DMSO was constant at a final concentration of 1%.

4) Test compounds were incubated with cells in duplicate for 2 h at 37° C/5% CO2 in a humidified atmosphere.
5) The media was removed and cells were lysed by freeze-thawing in cell lysis buffer.
6) Detection of phosphorylated S6Ser235/236 was then carried out using a PathScan ELISA kit (Cell Signaling Technology #7205).
7) Lysates were diluted 1:1 with sample diluent before being applied to wells coated with an antibody against phosphorylated-S6 protein.
8) The ELISA was then performed as stated in the manufacturers' instructions.
9) The raw data were normalised to control values and analysed using a 4-parameter logistic equation in GraphPad Prism.

The $IC_{50}$ values obtained for the compounds tested are set out in the table below.

(c) MCF-7 Proliferation Assays

The following assay was used to determine the ability of test compounds to inhibit cell growth.

Protocol:

The following protocol was used:
1) MCF-7 cells were seeded in 96-well plates at 5000 cells per well and allowed to adhere overnight prior to addition of compound or vehicle control.
2) Test compounds were prepared from 10 mM DMSO stocks to give a final concentration range of 100 μM, 30 μM, 10 μM, 3 μM, 1 μM, 0.3 μM, 0.1 μM, 0.03 μM, 0.01 μM and vehicle control. The DMSO content was constant at 1%.
3) Test compounds were incubated with the cells for 72 h at 37° C. 5% CO2 in a humidified atmosphere.
4) Alamar blue 10% (v/v) was then added and incubated for a further 6 h, and fluorescent product detected using the BMG FLUOstar plate reader.
5) Data were analysed using a 4-parameter logistic equation in GraphPad Prism.

The $IC_{50}$ values obtained for the compounds tested are set out in the table below.

(d) Evaluation of Brain and Plasma Concentrations in an In Vivo Cassette Mouse Model The compounds of this invention were evaluated in an in vivo cassette mouse model to determine brain and plasma concentrations following oral dosing. This is an industry-standard and recognised means to assess brain penetration of small molecules (for recent literature article, refer to In vitro permeability analysis, pharmacokinetic and brain distribution study in mice of imperatorin, isoimperatorin and cnidilin in Radix Angelicae Dahuricae, Fitoterapia, Volume 85, March 2013, Pages 144-153). It is also recognised that higher brain concentrations (and higher ratios of brain: plasma concentration) lead to greater exposure in the brain—this is clearly advantageous if the brain is the site of action.

Experimental Method:

For a single cassette study, male CD-1 mice were used (n=3 per timepoint, two timepoints: 1.0 hr and 3.0 hr).

5 compounds were dosed PO per cassette (dose level 2.5 mg/kg per compound, dose conc. 0.25 mg/ml, dose volume 10.0 ml/kg).

Formulation used to solubilize compounds: 10% DMSO/90% hydroxypropyl-β-cyclodextrin (20% w/v aqueous)

Sampling was terminal and plasma and brain matrices were generated. To prepare plasma samples, protein was precipitated using acetonitrile. To prepare brain samples, homogenisation and protein precipitation was performed with acetonitrile. Samples were analysed using HPLC-TOF MS using electrospray ionisation.

The brain and plasma concentrations and brain-plasma ratios observed for the compounds tested are set out in the table below.

| Example No. | (a) p70S6K1 $IC_{50}$ (μM) | (b) MCF-7 pS6 ELISA $IC_{50}$ (μM) | (c) MCF-7 proliferation $IC_{50}$ (μM) | (d) Plasma conc. at 3 hours (μM) | (d) Brain conc. at 3 hours (μM) | (d) Brain:Plasma ratio at 3 hours |
|---|---|---|---|---|---|---|
| 1 | 0.004 | 3.000 | 12.200 | 0.97 | 3.65 | 3.8 |
| 2 | 0.025 | 0.400 | 15.000 | 1.23 | 1.50 | 1.2 |
| 3 | 0.026 | 3.200 | 5.300 | 0.52 | 0.59 | 1.1 |
| 4 | 0.030 | 0.400 | 2.300 | 1.73 | 1.08 | 0.6 |
| 5 | 0.012 | 3.200 | 33.000 | 0.76 | 2.48 | 3.3 |
| 6 | 0.033 | — | 28.000 | 0.55 | 2.38 | 4.3 |
| 7 | 0.009 | 0.900 | 7.000 | 0.83 | 2.88 | 3.5 |
| 8 | 0.026 | 1.400 | 24.000 | 0.76 | 0.82 | 1.1 |
| 9 | 0.003 | 0.300 | 15.000 | 1.51 | 2.07 | 1.4 |
| 10 | 0.062 | — | — | 0.18 | 0.75 | 4.2 |
| 11 | 0.064 | — | ND | 0.35 | 2.62 | 7.5 |
| 12 | 0.007 | 0.800 | 8.400 | 5.05 | 2.40 | 0.5 |
| 13 | 0.005 | 1.200 | ND | 0.70 | 2.96 | 4.2 |
| 14 | 0.009 | 0.900 | 9.000 | 0.79 | 2.65 | 3.3 |
| 15 | 0.006 | 0.500 | 12.000 | 1.19 | 2.43 | 2.0 |
| 16 | 0.018 | 57% inhibition at 0.3 uM | 4.200 | 3.34 | 3.25 | 1.0 |
| 17 | 0.032 | ND | — | 0.16 | 0.21 | 1.3 |
| 18 | 0.012 | 5.04^ | — | 0.56 | 0.99 | 1.8 |
| 19 | 0.022 | 4.59^ | — | 0.81 | 2.33 | 2.9 |

"—" indicates compound was not tested in that assay
"ND" indicates an $IC_{50}$ could not be determined.
"^" indicates compounds were tested in a MCF7 pS6 ELISA assay as described herein except that (a) the phosphorylation of S6 at the Serine residues 240 and 244 was detected (using Abcam™ PhosphoTracer S6 RP (pS240/244) ELISA Kit, abcam #ab119644) rather than Serine residues 235 and 236 and (b) 0% FBS was used rather than 1% FBS.

In summary, the compounds of the invention demonstrate potent inhibition of p70S6K1. The compounds exhibit cellular activity. The compounds tested exhibit favourable brain and plasma concentrations in mice following oral dosing, with brain concentrations in excess of plasma, leading to high brain: plasma ratios. It is generally considered that brain: plasma ratio of >0.5 is favourable for treatment of diseases of the brain.

(e) Evaluation of Efficacy of Compounds in Counteracting Tumour Initiation and Metastasis in an In Vivo Model of Triple Negative Breast Cancer (TNBC)

It is known that S6K1 has a crucial role in the recurrence of TNBC cancers following surgery, mainly through the activity of S6K1 in promoting survival of cancer cells in the host via phosphorylation and activation of the anti-apoptotic protein Bcl2 and of Gli1 (Belletti 2014). In addition, S6K1 promotes metastasis of TNBC cells (Akar 2010, Hung 2014).

In order to test the efficacy of an inhibitor of S6K1 in an in vivo model of tumour initiation and metastasis, the following experiment was established:

A total of 30 female athymic nude mice (Hsd:Athymic Nude-Foxn1$^{nu}$) were purchased from Harlan (UK) and acclimatised for 7 days prior to study commencement. Animals were housed in IVC cages (5 per cage) with individual mice identified by ear punch. All animals were allowed free access to a standard certified commercial diet and sanitised water during the study. The holding room was maintained under standard conditions: 20-24° C., 40-70% humidity and a 12 h light/dark cycle.

On day −1, animals were randomly assigned to treatment groups as indicated in the table below, and drug treatment commenced. On day 0, MDA-MB-231 cells (1×10⁶ in matrigel) were implanted into the second mammary fat pad.

The dosing route was PO and the formulation was as follows: 10% DMSO/90% hydroxypropyl-β-cyclodextrin (20% w/v aqueous)

Treatment Groups:

| Group | n | Treatment | Dose | Dosing route | Dosing schedule | Dosing period (days) |
|---|---|---|---|---|---|---|
| 1 | 10 | Vehicle only | — | p.o. | QD | 21 |
| 3 | 15 | Example 15 | 250 mg/kg | p.o. | QD | 21 |

During the experiment, the following outcome measures were assessed:

(1) Time to palpation of tumour (latency) (2) tumour volume (3) tumour and organ weights as a measure of metastasis (4) visual appearance of metastatic nodules in the lungs Outcomes:

(1) Time to Palpation of Tumour

The compound of Example 15 delays time until appearance (palpation) of tumour and also decreases the rate of incidence (see FIG. 1).

(2) Tumour Volume

Figure 2:
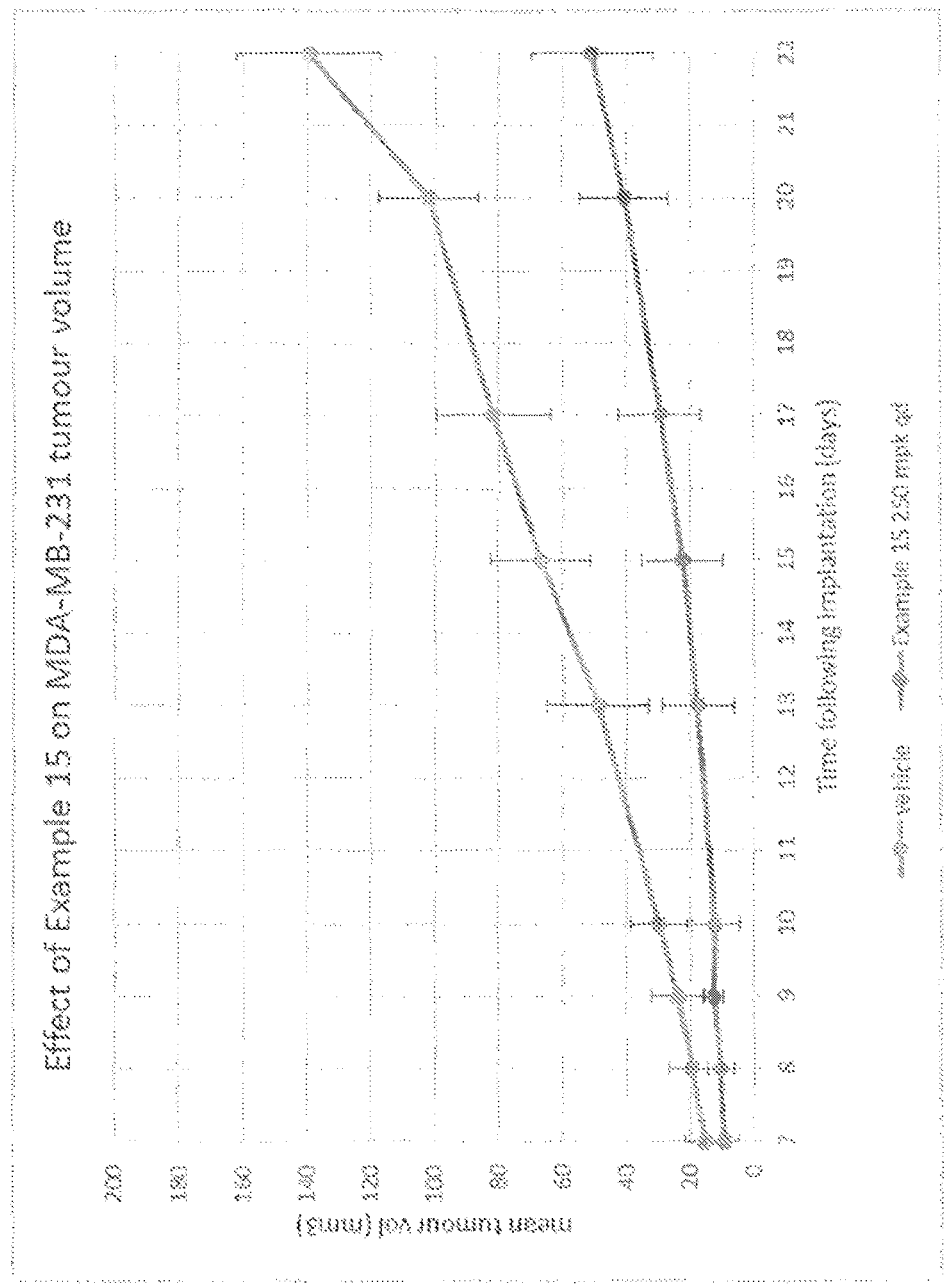
FIG. 2 is a plot of mean MDA-MB-231 tumour volume versus time after implantation in test animals treated with the compound of Example 15 or a vehicle control.

Example 15 induces a reduction in volume of tumours which is statistically significant over vehicle (p<0.05) as determined by multiple t-tests with the statistical significance determined using the Sidak-Bonferroni method. The lung and tumour weights were taken and provide a measure of the extent of metastasis (see FIG. 2).

At day 21 the lungs and tumour of vehicle and treated groups were weighed.

Figure 4:
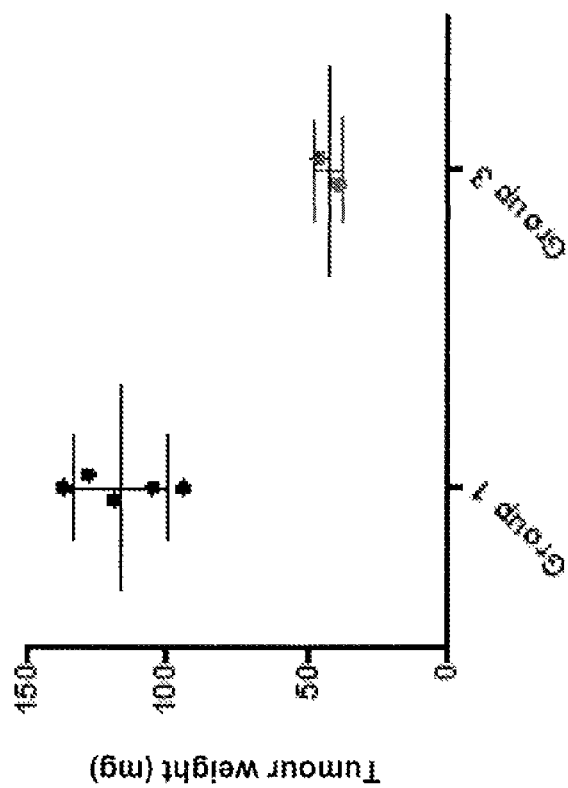
FIG. 4 shows the tumour weight after 21 days in the vehicle control group of test animals and the group of test animals treated with the compound of Example 15.
Figure 3:
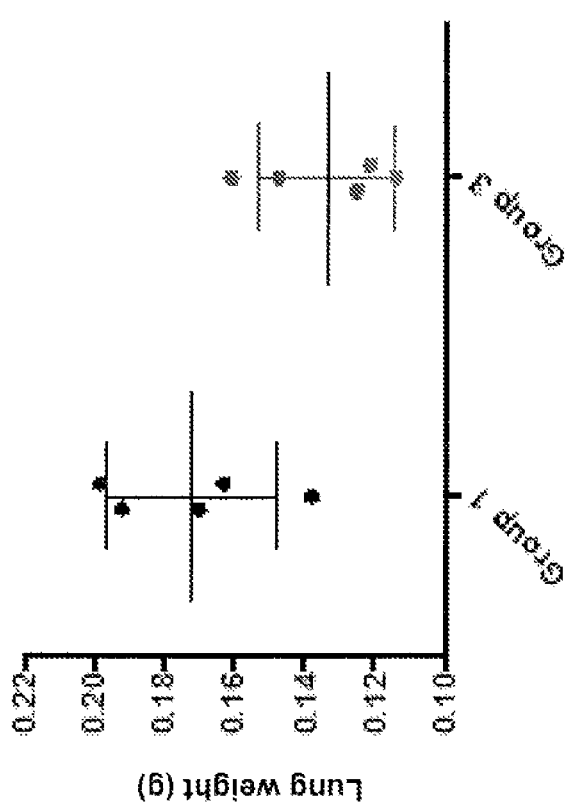
FIG. 3 shows the lung weight after 21 days in the vehicle control group of test animals and the group of test animals treated with the compound of Example 15.

Treatment with the compound of Example 15 led to a reduction in weight of lungs compared to the vehicle treated group which indicates a reduction in metastatic lesions for the treatment group (see FIG. 3). In addition, the tumours from the treated animals weighed significantly less (see FIG. 4).

(3) Visual Appearance of Metastatic Nodules in the Lungs

At necroscopy the lungs of the vehicle and treated animals were examined for presence of metastatic nodules:

| Group no. | Treatment | Dose | No. mice bearing visible lung mets nodules | Mean no. of nodules per lung |
|---|---|---|---|---|
| 1 | Vehicle only | — | 3/5 (60%) | 3 |
| 3 | Example 15 | 250 mg/kg QD × 21 | 1/5 (20%) | 1 |

This shows that example 15 is effective in reducing the metastatic burden in the lungs of the mouse arising as spontaneous metastasis from a TNBC primary tumour.

Taken together this indicates that Example 15, an S6K1 inhibitor, is effective in (a) preventing tumour initiation (b) limiting the growth of tumours that do present and (c) preventing metastasis to the lung arising from the primary tumour.

(f) Evaluation of Compounds in the Audiogenic Seizure Assay, an In Vivo Model of Fragile X Syndrome (FXS)

Seizures occur in conjunction with FXS and autism in up to one-quarter of children with these disorders (Berry-Kravis E (2002) Epilepsy in fragile X syndrome. Dev. Med. Child Neurol. 44(11):724-728). Increased susceptibility to sound-induced seizures, called audiogenic seizures (AGS), is a robust and reliable phenotype in FXS mice (Fmr1 KO) that does not occur in WT mice. The audiogenic seizure assay (AGS) is a well documented mouse model of FXS (Audiogenic seizures susceptibility in transgenic mice with fragile X syndrome, Epilepsia. 2000 January; 41(1):19-23). In such a model it is possible to dose compounds to observe effects on susceptibility of the mice to audiogenic seizures. The following AGS experiment was set up to test the efficacy of compounds of this application:

The following experiment design was used:

| Group | Mice | n | treatment | Dosing |
|---|---|---|---|---|
| 1 | FXS (Fmr1 KO) | 10 | vehicle | QD × 7 PO |
| 2 | FXS (Fmr1 KO) | 10 | Example 15, 25 mg/kg | QD × 7 PO |

Strain of FXS Mouse Used: FVB Background

Vehicle used: 10% DMSO/90% hydroxypropyl-β-cyclodextrin (20% w/v aqueous)

Animals were assessed in AGS following 7 consecutive days of dosing.

Method:

The experimental chamber consisted of a plastic cage of dimensions 25×25×47 cm in which a doorbell (Electrical bell Heath Zenith, model 172C-A) had been mounted on the cage roof.

Mice were taken from their housing room one by one and transferred into the experimental chamber and allowed to explore the novel environment (basal noise ~65 dB) for a period of 30 seconds after which point the bell was rung (124 dB).

The resulting motor responses were classified using a scale modified from the one originally described by Jobe et al. (1973): no response (NR: pause or continuous exploration), wild running (WR), clonic seizure (CS), tonic seizure (TS), respiratory arrest and/or death (RA). In order to define the intensity of the behavioral response a seizure severity score was used (SSS) (Musumeci et al., 2000), consisting of a score assigned to each animal depending on its behavioral response (NR=0, WR=1, CS=2, TS=3, RA=4). To determine the SSS for a treatment group the scores of the individual mice are summed. The motor response rate is defined as the percentage of animals per group responding to the stimulus.

Results:

| Group | NR | WR | CS | TS | RA | SSS | Motor Response rate (%) |
|---|---|---|---|---|---|---|---|
| 1 | 0 | 5 | 1 | 2 | 0 | 11 | 9/9 (100%) |
| 2 | 6 | 2 | 0 | 0 | 0 | 2 | 2/8 (25%) |

The data show that the incidence of audiogenic seizures and severity of response were both reduced by administration of Example 15 (statistically significant, p<0.01 by Fisher's test).

(g) Control of Brain Metastases Arising from Triple Negative Breast Cancer Cell Line MDA-MB-231

Triple negative breast cancers (TNBC) are recognised as being more likely to spread (metastasize) to the brain (Cancer, Volume 113, Issue 10, pages 2638-2645, 15 Nov. 2008, DOI: 10.1002/cncr.23930). It is also known that S6K1 promotes metastasis of TNBC cells (Akar 2010, Hung 2014).

In order to test the efficacy of an inhibitor of S6K1 in preventing brain metastases arising from TNBC cells, an in vivo mouse model was established:

Method:

Using a luciferase-tagged TNBC cell line (MDA-MB-231 (luc)) it was possible to track the spread of metastatic cells to the brain and other major organs via mouse whole-body imaging.

The MDA-MB-231(luc) cell-line was derived from MDA-MB-231 cells originally purchased from ATCC. These cells were stably transfected with pGL4.51 (Promega) using Lipofectamine 2000 (Life Technologies). Stably transfected colonies were selected for using neomycin and the most highly expressing clone was expanded. The cells have similar in vivo growth characteristics as the parental MDA-MB-231 cells.

Female athymic mice (Hsd:Athymic Nude-Foxn1$^{nu}$) were purchased from Harlan (UK) and acclimatised for 7 days prior to study commencement. Animals were housed in Individually Ventilated Cages (IVCs) (5 per cage) with individual mice identified by tail marking. All animals were allowed free access to a standard certified commercial diet and sanitised water during the study. The holding room was maintained under standard conditions: 20-24° C., 40-70% humidity and a 12 h light/dark cycle.

On day −1 with respect to inoculation of tumour cells, animals were randomly assigned to treatment groups as indicated in the following table:

| Group | n | Treatment | Dose | Dosing route | Dosing schedule | Dosing period |
|---|---|---|---|---|---|---|
| 1 | 5 | Vehicle only | Not applicable | p.o. | QD | 70 days |
| 2 | 5 | Example 15 | 125 mg/kg | p.o. | BID | 70 days |

The dosing route was p.o. and the formulation was as follows: 10% DMSO/90% hydroxypropyl-β-cyclodextrin (20% w/v aqueous)

On day 0 animals were anaesthetized and injected with 1×10$^5$ MDA-MB-231 (luc) cells directly into the heart. Intra-cardiac injection was chosen as this method leads to brain metastases. On day +1 animals were imaged using a Xenogen IVIS machine (following IP injection of 150 mg/kg) of D-luciferin). Evidence of light only in the cardiac area was indicative of a failed implantation and these animals were removed from the study. The experiment was commenced with 7 animals per treatment group to guarantee 5 animals per group completed the study.

Animals were imaged on 3 occasions during the study: 24 hours following intracardiac injection, 35 days after implantation and at the end of the study (70 days after implantation). For imaging, animals were first injected i.p. with D-luciferin (150 mg/kg) and 10 minutes later the animals were imaged under anaesthesia.

Results:

Whole body Imaging at 35 days revealed that 4 out of 5 vehicle-treated animals had visible metastatic spread while 0 out of 5 animals treated with Example 15 had visible metastases.

At the end of the 70 days, animals were imaged using the same method as described at 35 days. Following this the animals were then sacrificed and brain, liver and lungs were removed and imaged individually for metastatic spread. The results are displayed in the following table:

| Treatment | Dose (mg/kg) | Dosing route | Dosing period (days) | No. deaths on study | Incidence of metastasis Lung (%) | Liver (%) | Brain (%) |
|---|---|---|---|---|---|---|---|
| 5 Vehicle | — | p.o. | QD x 70 | 1 | 100 | 100 | 60 |
| 5 Example 15 | 125 | p.o. | BID x 70 | 0 | 40 | 0 | 0 |

In conclusion, Example 15 is highly effective in reducing the incidence of metastasis of Triple negative breast cancer cells (MDA-MB-231) to brain, liver and lung of nude mice as compared to vehicle treated mice. In particular, no evidence of brain metastasis was observed in the treated mice, indicating the effectiveness of Example 15 in penetrating the brain and exerting desired effect. In addition, Example 15 is well-tolerated, with 70 consecutive days of BID dosing and no treatment related deaths or adverse clinical signs observed.

Example 21

Pharmaceutical Formulations (i) Tablet Formulation

A tablet composition containing a compound of the formula (1) as defined in any one of Embodiments 1.0 to 1.57 may be prepared by mixing 50 mg of the compound with 197 mg of lactose (BP) as diluent, and 3 mg magnesium stearate as a lubricant and compressing to form a tablet in known manner.

(ii) Capsule Formulation

A capsule formulation is prepared by mixing 100 mg of a compound of the formula (1) as defined in any one of Embodiments 1.0 to 1.57 with 100 mg lactose and filling the resulting mixture into standard opaque hard gelatin capsules.

(iii) Injectable Formulation I

A parenteral composition for administration by injection can be prepared by dissolving a compound of the formula (1) as defined in any one of Embodiments 1.0 to 1.57 in water containing 10% propylene glycol to give a concentration of active compound of 1.5% by weight. The solution is then sterilised by filtration, filled into an ampoule and sealed.

(iv) Injectable Formulation II

A parenteral composition for injection is prepared by dissolving in water a compound of the formula (1) as defined in any one of Embodiments 1.0 to 1.57 (2 mg/ml) and mannitol (50 mg/ml), sterile filtering the solution and filling into sealable 1 ml vials or ampoules.

v) Injectable Formulation III

A formulation for i.v. delivery by injection or infusion can be prepared by dissolving the compound of formula (1) as defined in any one of Embodiments 1.0 to 1.57 (e.g. in a salt form) in water at 20 mg/ml. The vial is then sealed and sterilised by autoclaving.

vi) Injectable Formulation IV

A formulation for i.v. delivery by injection or infusion can be prepared by dissolving the compound of formula (1) as defined in any one of Embodiments 1.0 to 1.57 (e.g. in a salt form) in water containing a buffer (e.g. 0.2 M acetate pH 4.6) at 20 mg/ml. The vial is then sealed and sterilised by autoclaving.

(vii) Subcutaneous Injection Formulation

A composition for sub-cutaneous administration is prepared by mixing a compound of the formula (1) as defined in any one of Embodiments 1.0 to 1.57 with pharmaceutical grade corn oil to give a concentration of 5 mg/ml. The composition is sterilised and filled into a suitable container.

viii) Lyophilised Formulation

Aliquots of formulated compound of formula (1) as defined in any one of Embodiments 1.0 to 1.57 are put into 50 ml vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

Equivalents

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A method of treating a disease or condition selected from brain metastases from non-brain cancers in a subject in need thereof, which method comprising administering to the subject a therapeutically effective amount of a compound of the formula (1):

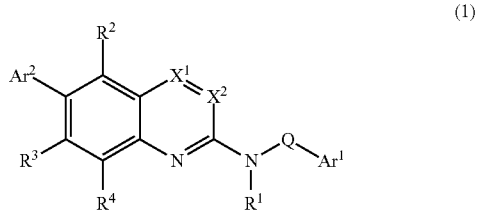

(1)

or a salt or tautomer thereof;
wherein:
$X^1$ is N or $N^+(O^-)$;
$X^2$ is N or CH;
Q is selected from a $C_{1-3}$ alkylene group, cyclopropane-1,1-diyl and cyclobutane-1,1-diyl;
$R^1$ is selected from hydrogen and $C_{1-4}$ alkyl;
$R^2$, $R^3$ and $R^4$ are the same or different and each is selected from hydrogen and fluorine;
$Ar^1$ is a benzene, thiophene, naphthyl or pyridine ring optionally substituted with 1, 2 or 3 substituents selected from fluorine; chlorine; bromine; $C_{1-4}$ hydrocarbyl; $C_{1-4}$ hydrocarbyloxy; trifluoromethyl; difluoromethyl; cyano; trifluoromethoxy; difluoromethoxy;
$Ar^2$ is a monocyclic 5- or 6-membered heteroaryl ring containing 1, 2 or 3 heteroatom ring members selected from O, N and S and being optionally substituted with 1, 2 or 3 substituents selected from fluorine; $C_{1-4}$ hydrocarbyl; amino; mono-$C_{1-4}$ hydrocarbylamino and di-$C_{1-4}$ hydrocarbylamino;
and wherein, in each substituent consisting of or containing $C_{1-4}$ hydrocarbyl, the $C_{1-4}$ hydrocarbyl is selected from $C_{1-4}$ alkyl, $C_{2-4}$ alkenyl, $C_{2-4}$ alkynyl, cyclopropyl, cyclobutyl and cyclopropylmethyl.

2. A method according to claim 1, wherein the compound is of the formula (1):

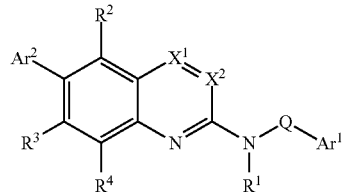

(I)

or a salt or tautomer thereof;
wherein:
$X^1$ is N or $N^+(O-)$;
$X^2$ is N or CH;
Q is a $C_{1-3}$ alkylene group;
$R^1$ is selected from hydrogen and $C_{1-4}$ alkyl;
$R^2$, $R^3$ and $R^4$ are the same or different and each is selected from hydrogen and fluorine;
$Ar^1$ is a benzene, thiophene, naphthyl or pyridine ring optionally substituted with 1, 2 or 3 substituents selected from fluorine; chlorine; bromine; $C_{1-4}$ hydrocarbyl; $C_{1-4}$ hydrocarbyloxy; trifluoromethyl; difluoromethyl; cyano; trifluoromethoxy; difluoromethoxy;
$Ar^2$ is a monocyclic 5- or 6-membered heteroaryl ring containing 1, 2 or 3 heteroatom ring members selected from O, N and S and being optionally substituted with 1, 2 or 3 substituents selected from fluorine; $C_{1-4}$ hydrocarbyl; amino; mono-$C_{1-4}$ hydrocarbylamino and di-$C_{1-4}$ hydrocarbylamino;
and wherein, in each sub stituent consisting of or containing $C_{1-4}$ hydrocarbyl, the $C_{1-4}$ hydrocarbyl is selected from $C_{1-4}$ alkyl, $C_{2-4}$ alkenyl, $C_{2-4}$ alkynyl, cyclopropyl and cyclopropylmethyl.

3. A method according to claim 1 wherein Q is $CH_2$ or $CH(CH_3)$.

4. A method according to claim 1 wherein wherein $X^1$ is N.

5. A method according to claim 1 wherein $X^2$ is N.

6. A method according to claim 1 wherein $X^2$ is CH.

7. A method according to claim 1 wherein $R^1$ is selected from hydrogen, methyl and ethyl.

8. A method according to claim 1 wherein $Ar^1$ is a benzene ring optionally substituted as defined in claim 1.

9. A method according to claim 8 wherein the optional substituents are selected from fluorine, chlorine, methyl and methoxy.

10. A method according to claim 9 wherein $Ar^1$ is selected from phenyl, 3-chlorophenyl, 3-fluorophenyl, 4-fluorophenyl, 3-methoxyphenyl, 3-methylphenyl and 3,4-difluorophenyl.

11. A method according to claim 1 wherein $R^2$ is hydrogen, $R^3$ is hydrogen and $R^4$ is hydrogen.

12. A method according to claim 11 wherein $Ar^2$ is a pyrazole ring optionally substituted as defined in claim 1.

13. A method according to claim 1 wherein $Ar^2$ is unsubstituted.

14. A method according to claim 2 wherein the compound is selected from:
Benzyl-methyl-[6-(1H-pyrazol-4-yl)-quinoxalin-2-yl]-amine;
(3-Chloro-benzyl)[6-(1H-pyrazol-4-yl)-quinoxalin-2-yl]-amine;
(4-Fluoro-benzyl)-[6-(1H-pyrazol-4-yl)-quinoxalin-2-yl]-amine;
(3-Methoxy-benzyl)[6-(1H-pyrazol-4-yl)-quinoxalin-2-yl]-amine;

(4-Fluoro-benzyl)-methyl-[6-(1H-pyrazol-4-yl)-quinoxalin-2-yl]-amine;
Benzyl-ethyl[6-(1H-pyrazol-4-yl)-quinoxalin-2-yl]-amine;
(3-Fluoro-benzyl)-methyl[6-(1H-pyrazol-4-yl)-quinoxalin-2-yl]-amine;
(3,4-Difluoro-benzyl)[6-(1H-pyrazol-4-yl)-quinoxalin-2-yl]-amine;
((R)-1-Phenyl-ethyl)[6-(1H-pyrazol-4-yl)-quinoxalin-2-yl]-amine;
((S)-1-Phenyl-ethyl)[6-(1H-pyrazol-4-yl)-quinoxalin-2-yl]-amine;
Benzyl-methyl[7-(1H-pyrazol-4-yl)-benzo[1,2,4]triazin-3-yl]-amine;
Benzyl-methyl[1-oxy-7-(1H-pyrazol-4-yl)-benzo[1,2,4]triazin-3-yl]-amine;
[(R)-1-(3-Methoxy-phenyl)-ethyl]-[6-(1H-pyrazol-4-yl)-quinoxalin-2-yl]-amine;
Methy(R)-1-phenyl-ethyl)[6-(1H-pyrazol-4-yl)-quinoxalin-2-yl]-amine;
Methyl-((S)-1-phenyl-ethyl)[6-(1H-pyrazol-4-yl)-quinoxalin-2-yl]-amine;
[(R)-1-(3-Methoxy-phenyl)-ethyl]-methyl-[6-(1H-pyrazol-4-yl)-quinoxalin-2-yl]-amine,
[(R)-1-(3-Chloro-phenyl)-ethyl]-[6-(1H-pyrazol-4-yl)-quinoxalin-2-yl]-amine;
[6-(1H-Pyrazol-4-yl)-quinoxalin-2-yl]-((R)-1-m-tolyl-ethyl)-amine hydrochloride;
Benzyl[1-oxy-7-(1H-pyrazol-4-yl)-benzo[1,2,4]triazin-3-yl]-amine;
1-oxido-N-[(1R)-1-phenylethyl]-7-(1H-pyrazol-4-yl)-1,2,4-benzotriazin-1-ium-3-amine; and
N-[(1R)-1-phenylethyl]-7-(1H-pyrazol-4-yl)-1,2,4-benzotriazin-3-amine;
and salts and tautomers thereof.

15. A method according to claim 14 wherein the disease or condition is selected from brain metastases from triple-negative breast cancer.

16. A method according to claim 1 wherein the disease or condition is selected from brain metastases from breast cancer.

17. A method according to claim 16 wherein the disease or condition is selected from
brain metastases from triple-negative breast cancer.

18. A method of treating a disease or condition selected from brain metastases from non-brain cancers in a subject in need thereof, which method comprising administering to the subject a therapeutically effective amount of a compound selected from 1-oxido-N-[(1R)-1-phenylethyl]-7-(1H-pyrazol-4-yl)-1,2,4-benzotriazin-1-ium-3-amine; and N-[(1R)-1-phenylethyl]-7-(1H-pyrazol-4-yl)-1,2,4-benzotriazin-3-amine; and salts and tautomers thereof.

19. A method according to claim 18 wherein the disease or condition is selected from brain metastases from breast cancer.

20. A method according to claim 19 wherein the disease or condition is selected from brain metastases from triple-negative breast cancer.

* * * * *